United States Patent [19]
Zadini et al.

[11] Patent Number: 5,312,361
[45] Date of Patent: May 17, 1994

[54] AUTOMATIC CANNULATION DEVICE

[76] Inventors: Filiberto P. Zadini, 16814 Rayen St., Sepulveda, Calif. 91343; Giorgio C. Zadini, 2237 Hilltop La., Camarillo, Calif. 93012

[21] Appl. No.: 929,182

[22] Filed: Aug. 10, 1992

Related U.S. Application Data

[63] Continuation-in-part of Ser. No. 834,161, Feb. 11, 1992, abandoned, which is a continuation-in-part of Ser. No. 759,157, Sep. 13, 1991, abandoned.

[51] Int. Cl.⁵ .............................................. A61M 5/178
[52] U.S. Cl. ....................................... 604/165; 606/170; 604/180; 604/233; 604/164; 604/177
[58] Field of Search .................. 604/157, 158, 161, 164, 604/165, 168, 171, 173, 174, 177, 180, 233; 606/167, 170

[56] References Cited

U.S. PATENT DOCUMENTS

| | | | |
|---|---|---|---|
| 2,137,132 | 9/1937 | Cooley | 128/276 |
| 2,710,000 | 6/1955 | Cromer | 128/2 |
| 3,572,334 | 3/1971 | Petterson | 128/214.4 |
| 3,595,230 | 6/1971 | Suyeoka | 128/214.4 |
| 3,677,296 | 7/1972 | Stein | 604/184 |
| 3,766,915 | 10/1973 | Rychlik | 128/214.4 |
| 3,811,441 | 5/1974 | Sarnoff | 604/201 |
| 3,906,946 | 9/1975 | Nordström | 128/214.4 |
| 3,916,892 | 11/1975 | Latham | 128/214 R |
| 3,995,619 | 12/1976 | Glatzer | 128/2 B |
| 4,013,080 | 3/1977 | Froning | 604/165 |
| 4,191,186 | 3/1980 | Keeler | 128/214.4 |
| 4,193,400 | 3/1980 | Loveless | 128/214.4 |
| 4,292,970 | 10/1981 | Hession | 128/214.4 |
| 4,326,541 | 4/1982 | Eckels | 604/201 |
| 4,340,068 | 7/1982 | Kaufman | 604/201 |
| 4,464,171 | 10/1984 | Garwin | 604/53 |
| 4,464,177 | 10/1984 | McGaughey | 604/168 |
| 4,475,902 | 10/1984 | Shubert | 604/95 |
| 4,487,603 | 12/1984 | McGaughey | 604/168 |
| 4,529,399 | 7/1985 | Groshong | 604/53 |
| 4,530,695 | 7/1985 | Phillips et al. | 604/134 |
| 4,601,710 | 7/1986 | Moll | 604/165 |
| 4,654,030 | 3/1987 | Moll et al. | 604/165 |
| 4,667,679 | 5/1987 | Sahota | 128/663 |
| 4,676,781 | 6/1987 | Phillips et al. | 604/189 |
| 4,767,407 | 10/1988 | Foran | 604/164 |
| 4,828,548 | 5/1989 | Walter | 604/164 |
| 4,904,240 | 2/1990 | Hoover | 604/167 |
| 4,944,728 | 6/1990 | Carrell | 604/164 |
| 4,966,589 | 10/1990 | Kaufman | 604/174 |
| 5,066,288 | 11/1991 | Deniega | 604/274 |
| 5,186,712 | 2/1993 | Kelso | 604/165 |

Primary Examiner—Randall L. Green
Assistant Examiner—Rob Clarke
Attorney, Agent, or Firm—Robert M. Sperry

[57] ABSTRACT

An improved intravascular catheter placement device, for the automatic insertion of intravascular catheter into the interior of blood vessels comprising a needle, an intravascular catheter concentric to the needle, and self-propelling means for moving said catheter into a blood vessel upon needle penetration of the wall of the blood vessel. The self-propelling means is actuated by means for sensing penetration of a blood vessel.

84 Claims, 41 Drawing Sheets

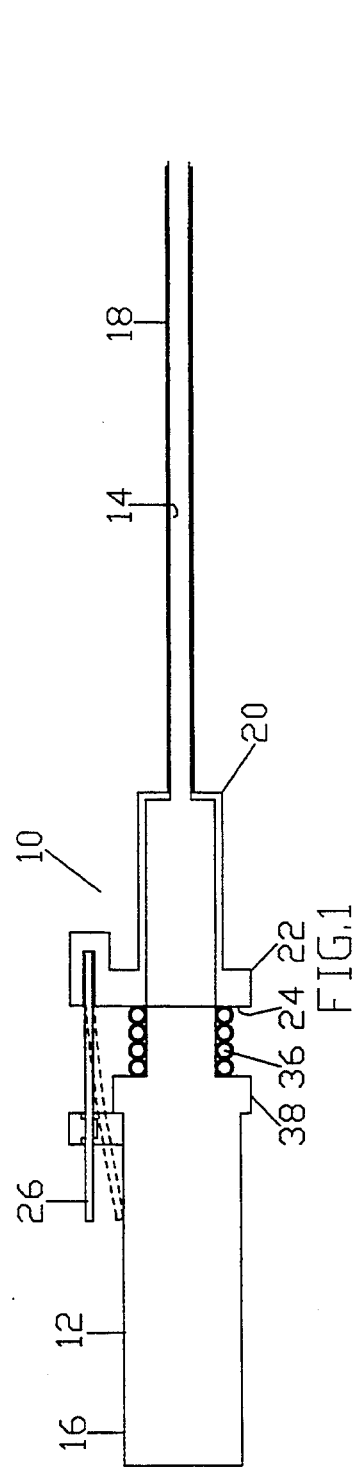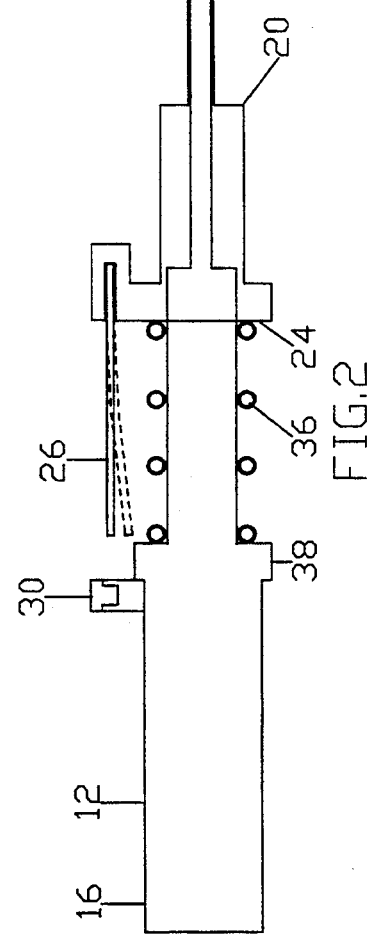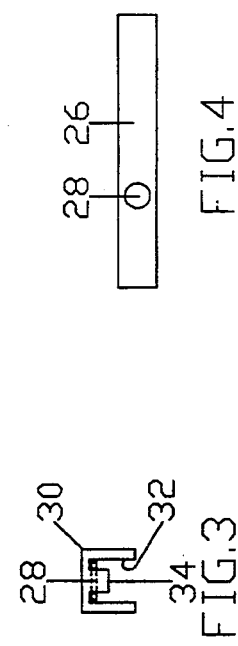

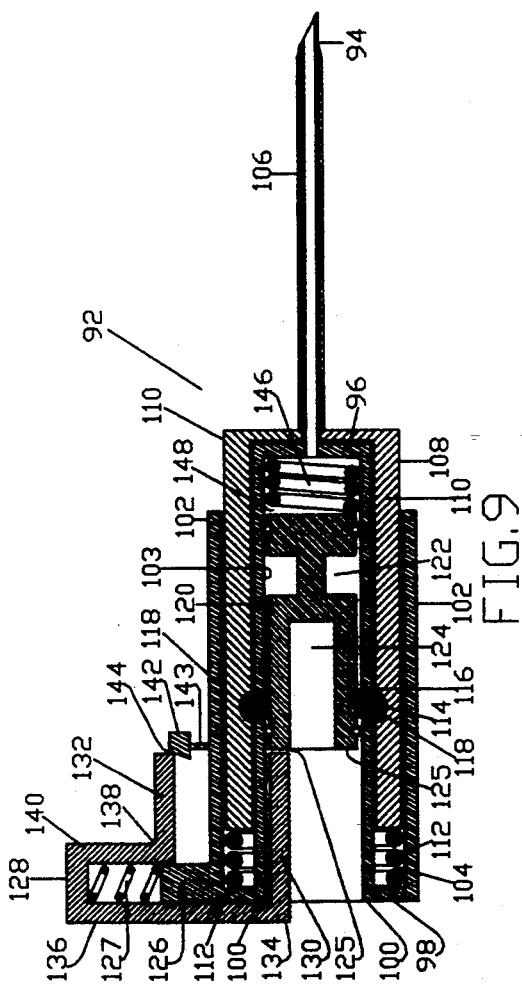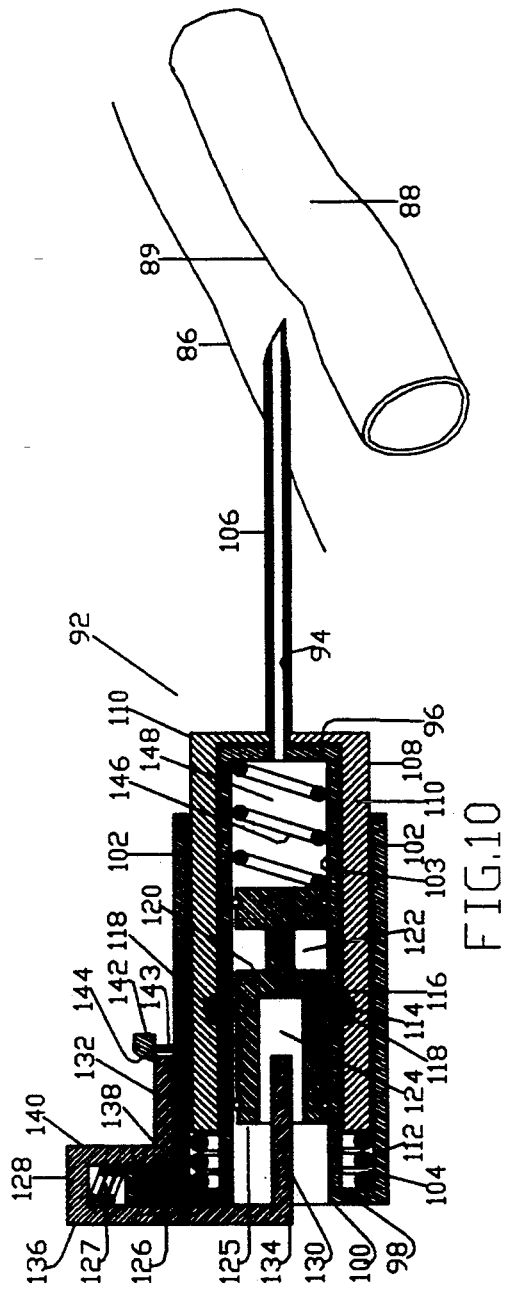

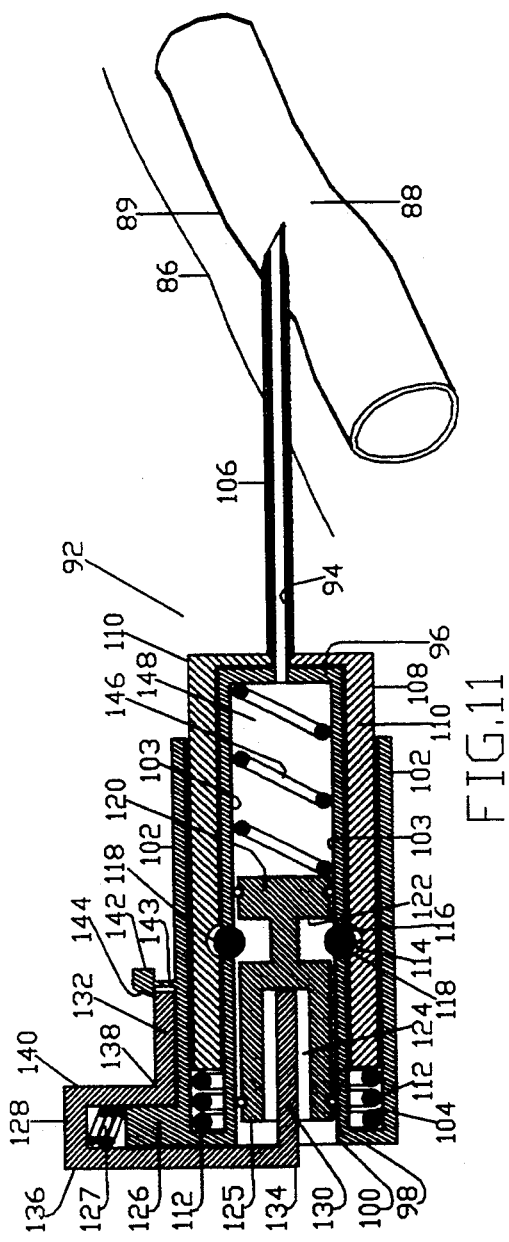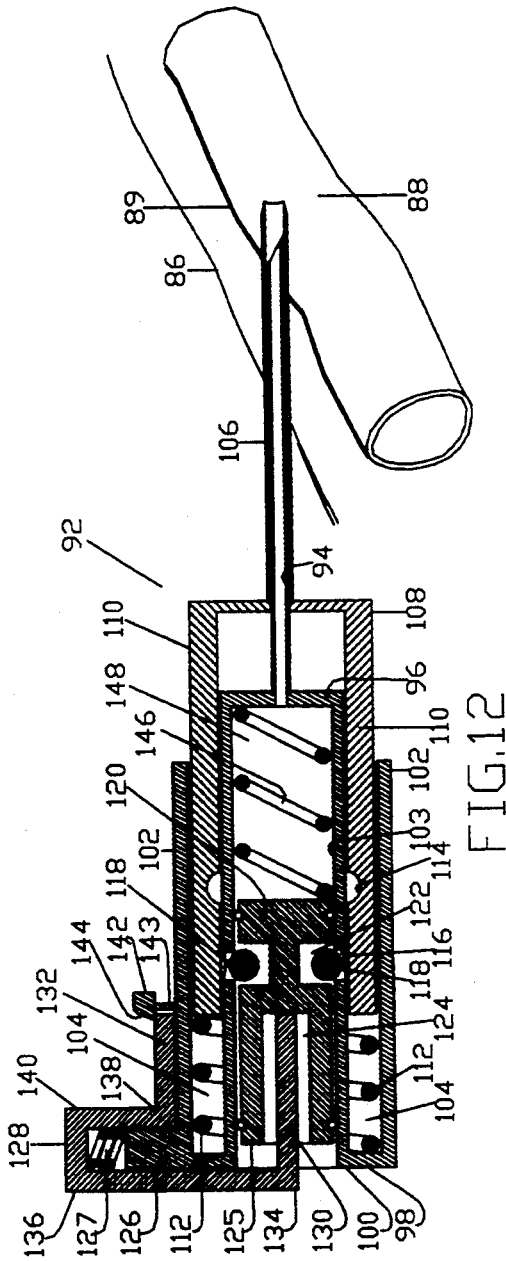

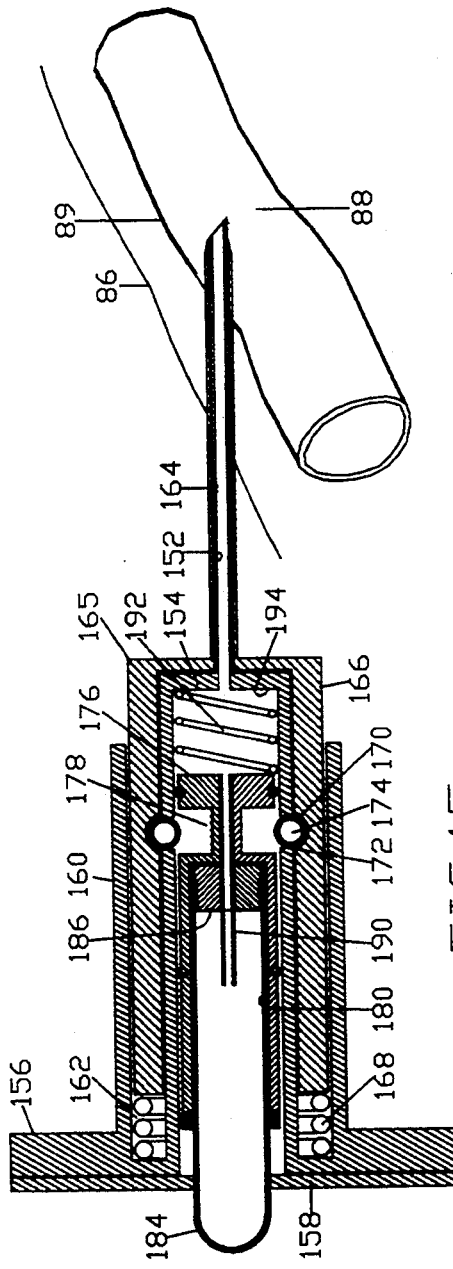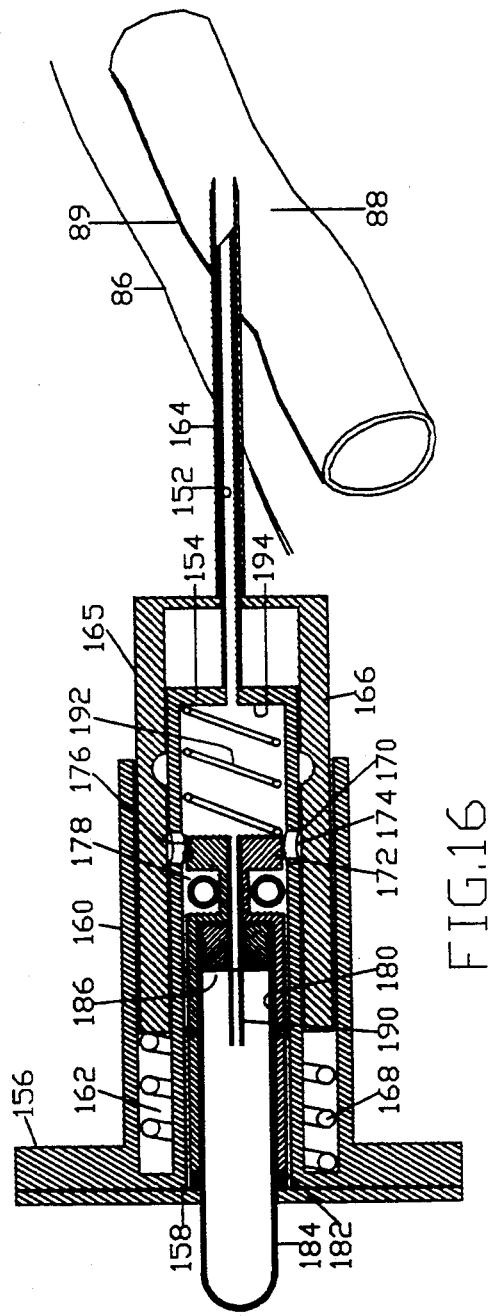

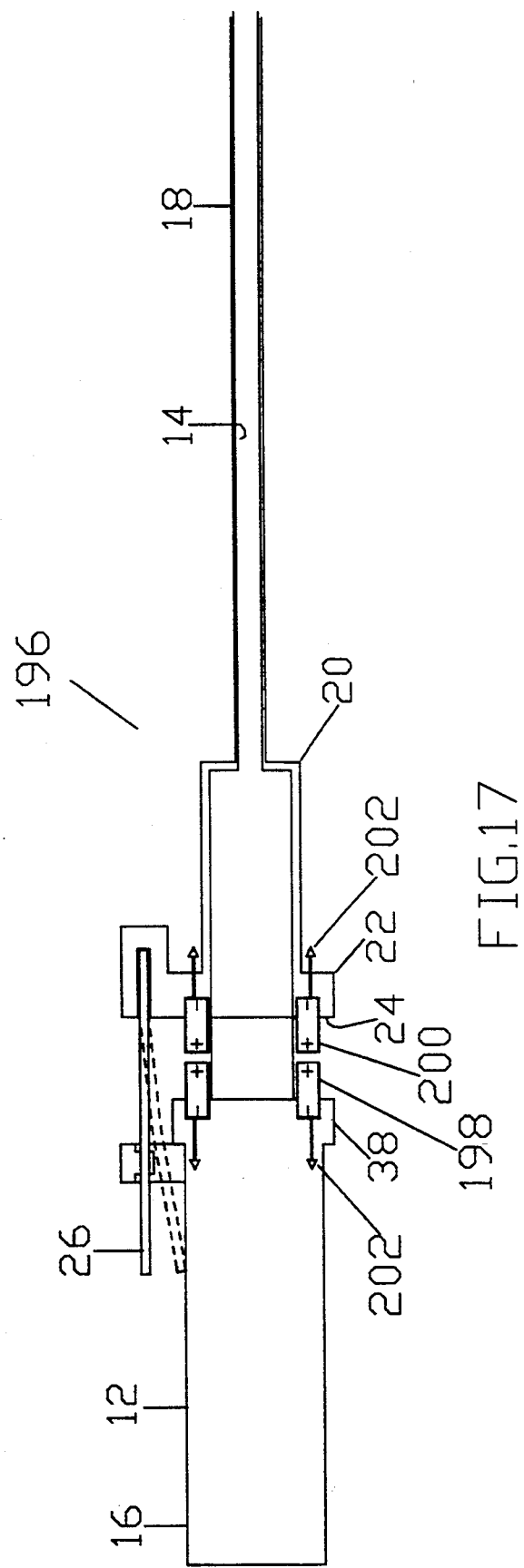

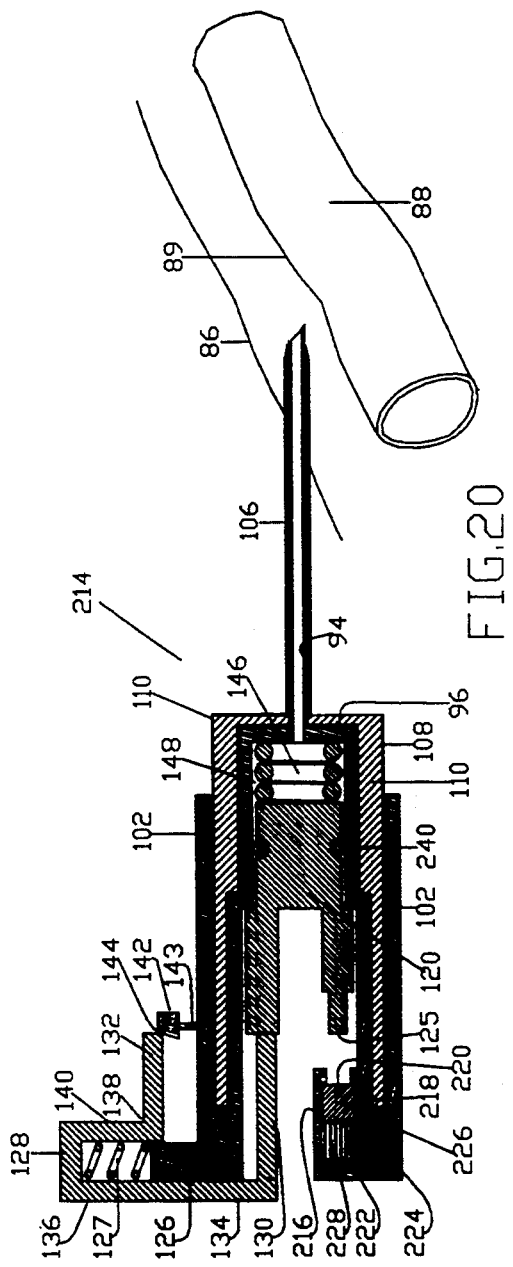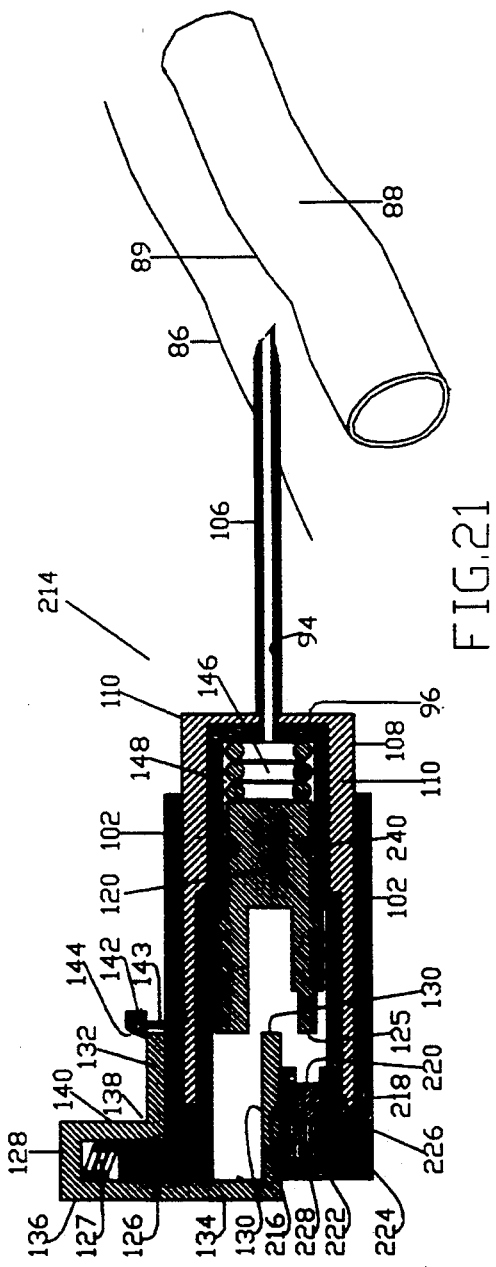

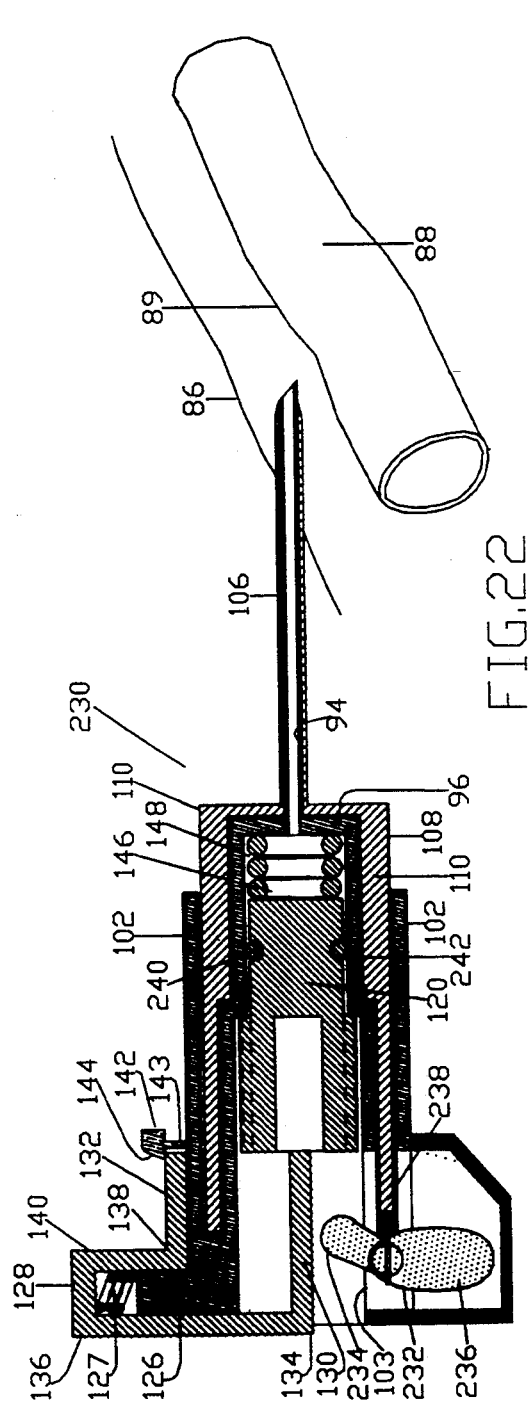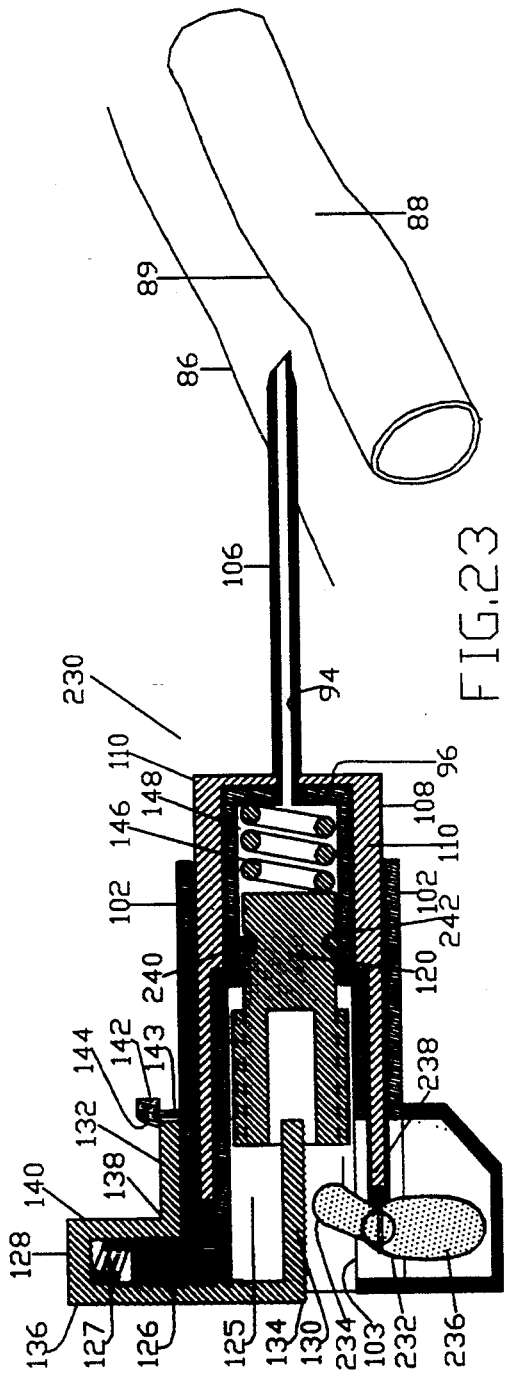

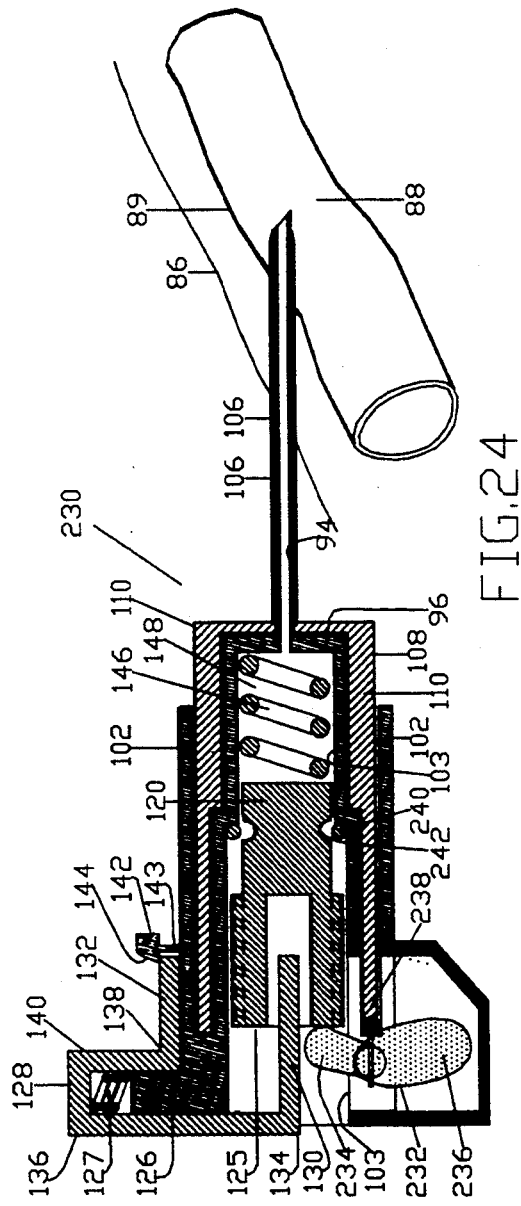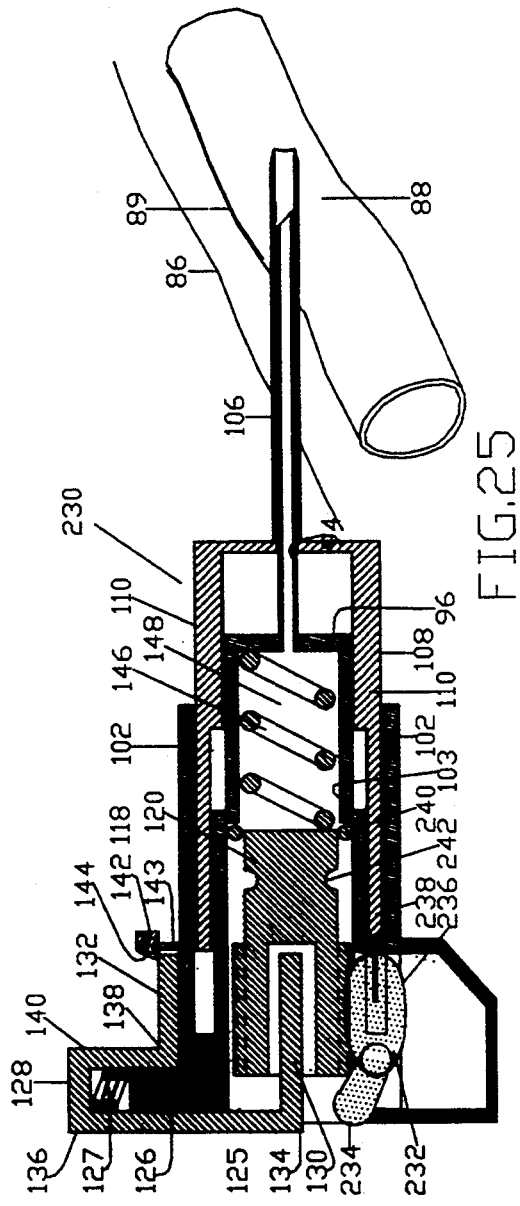

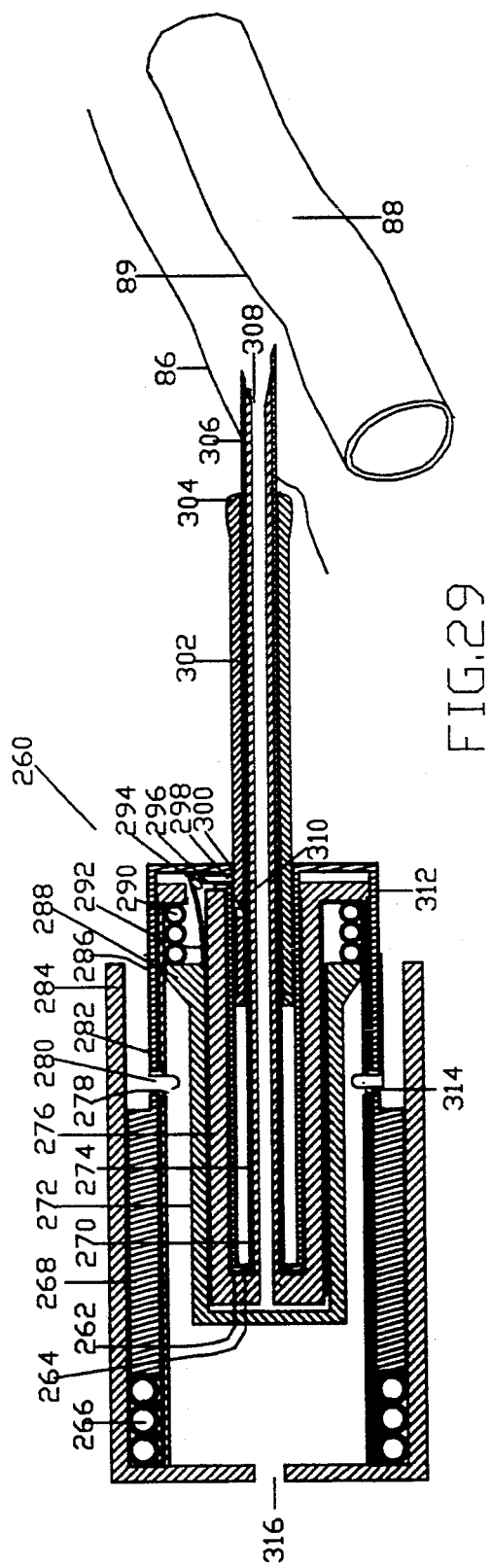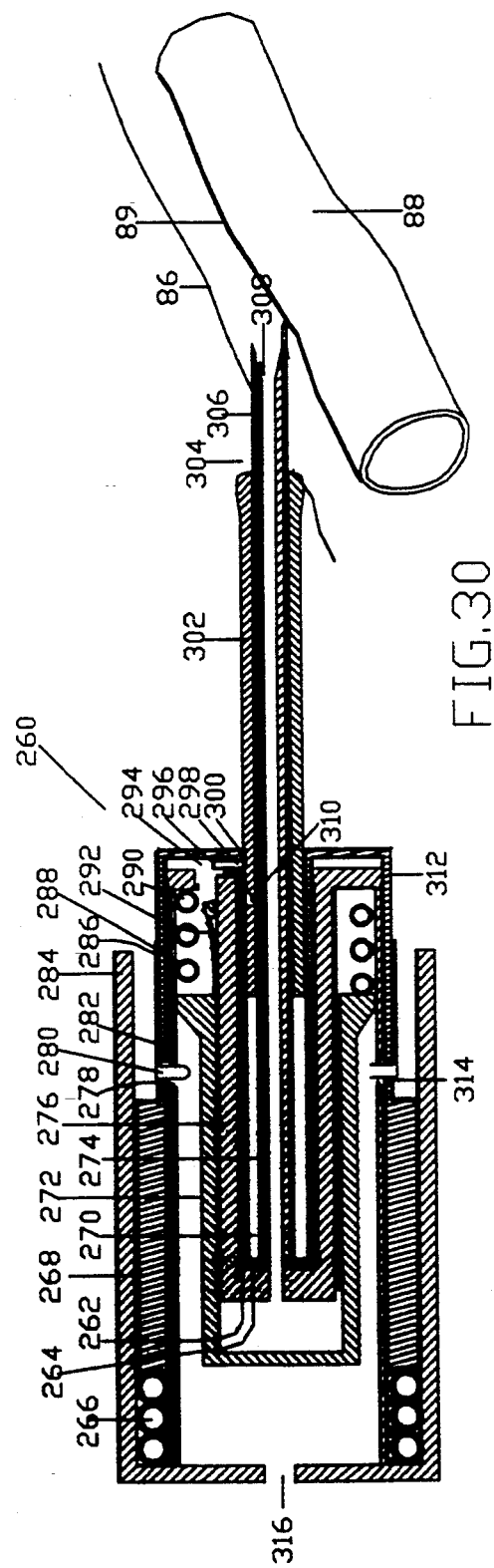

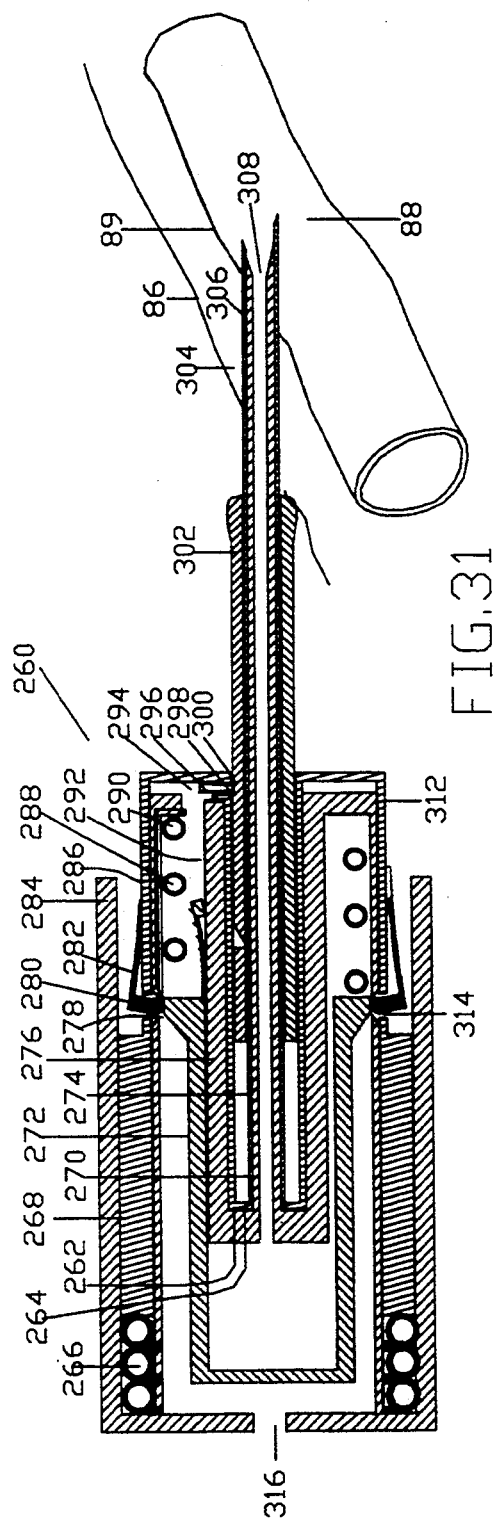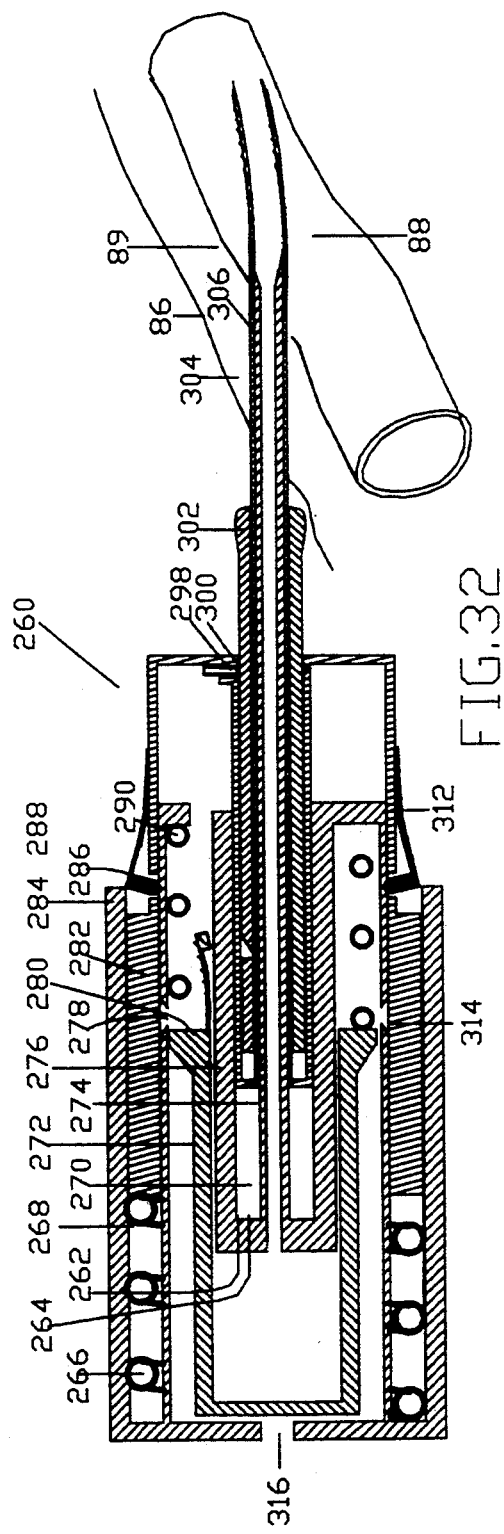

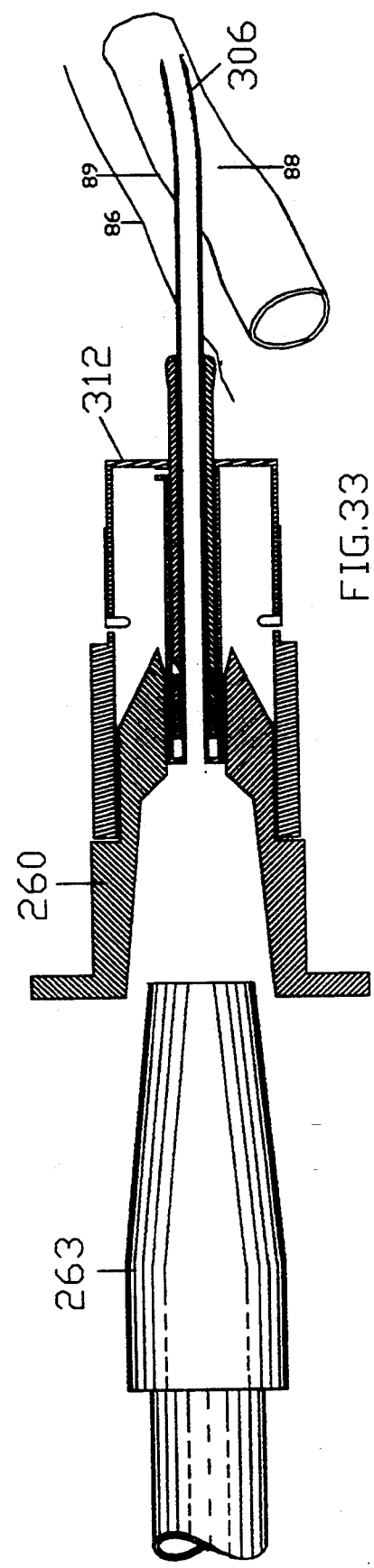

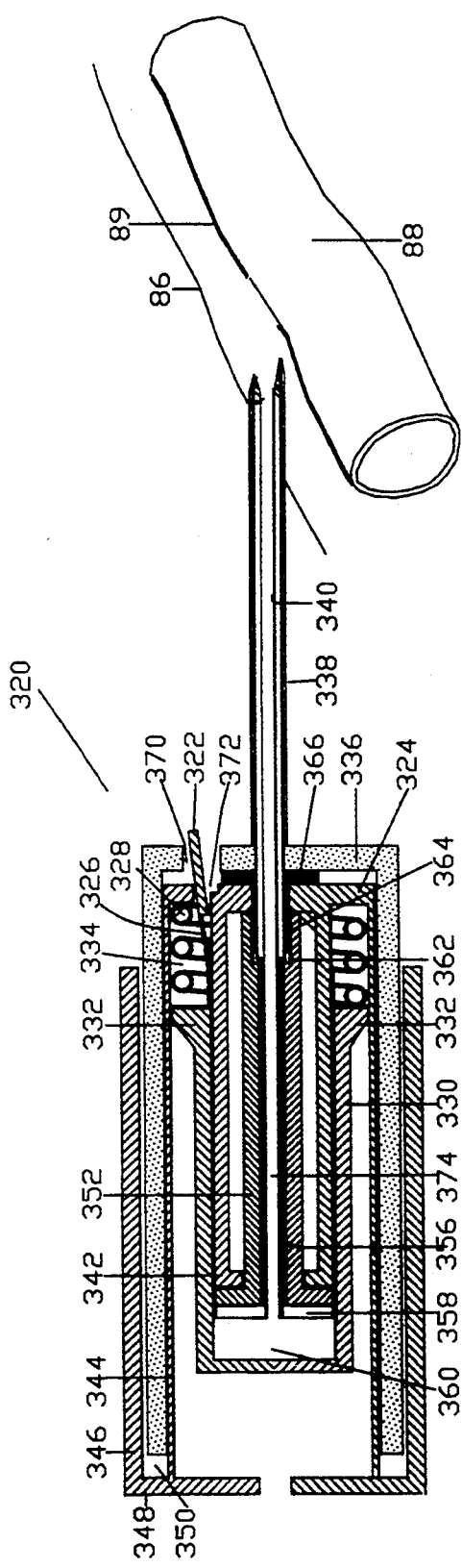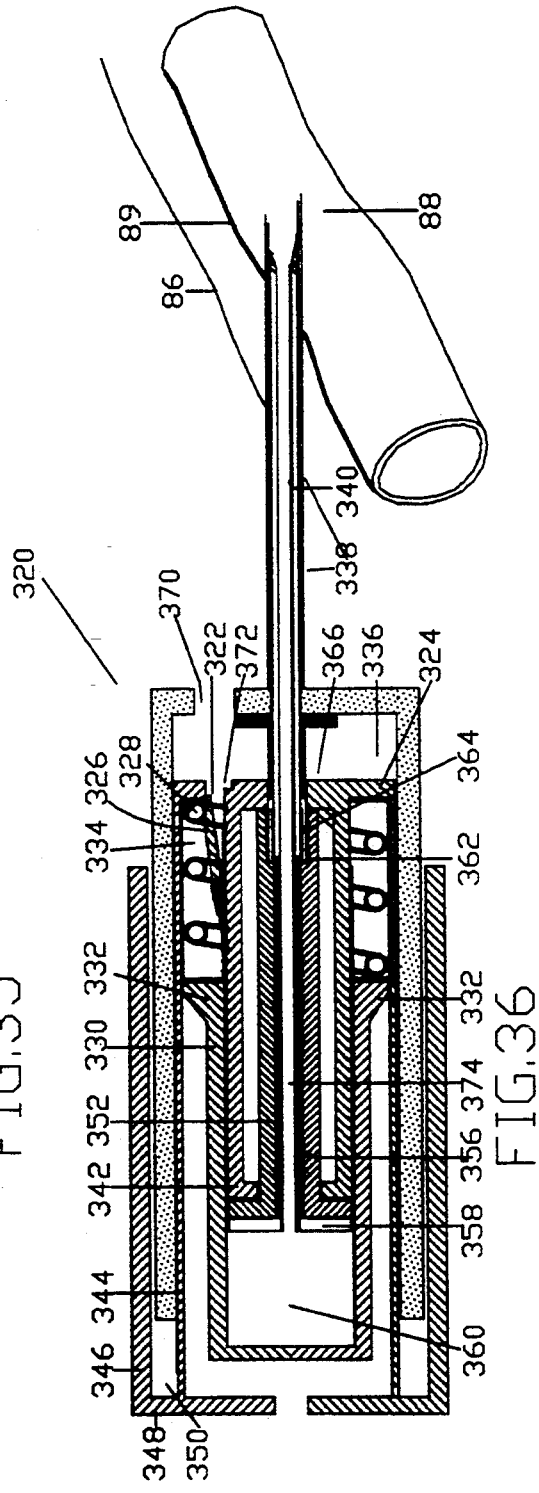

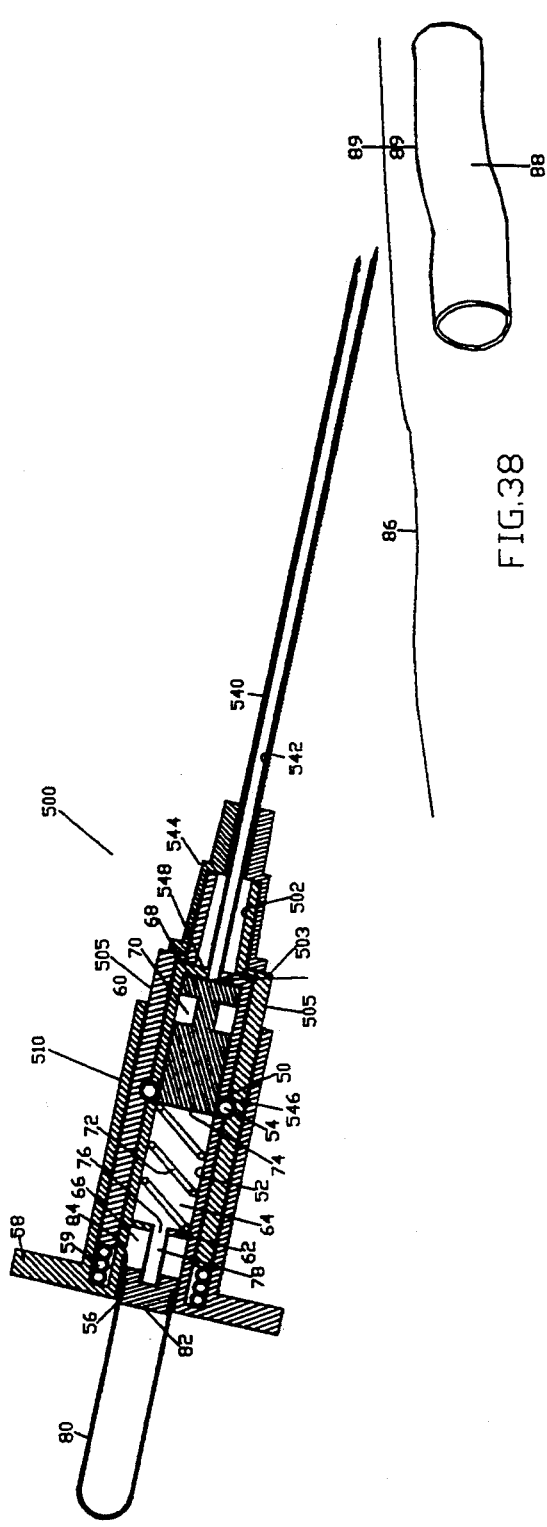
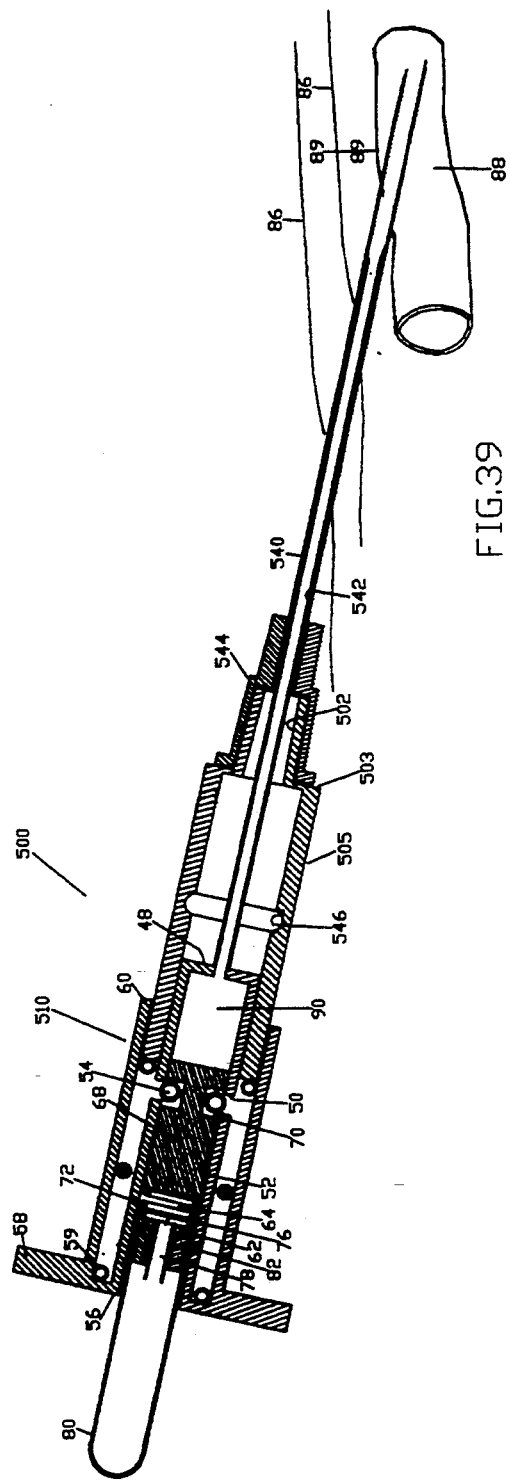
FIG.38
FIG.39

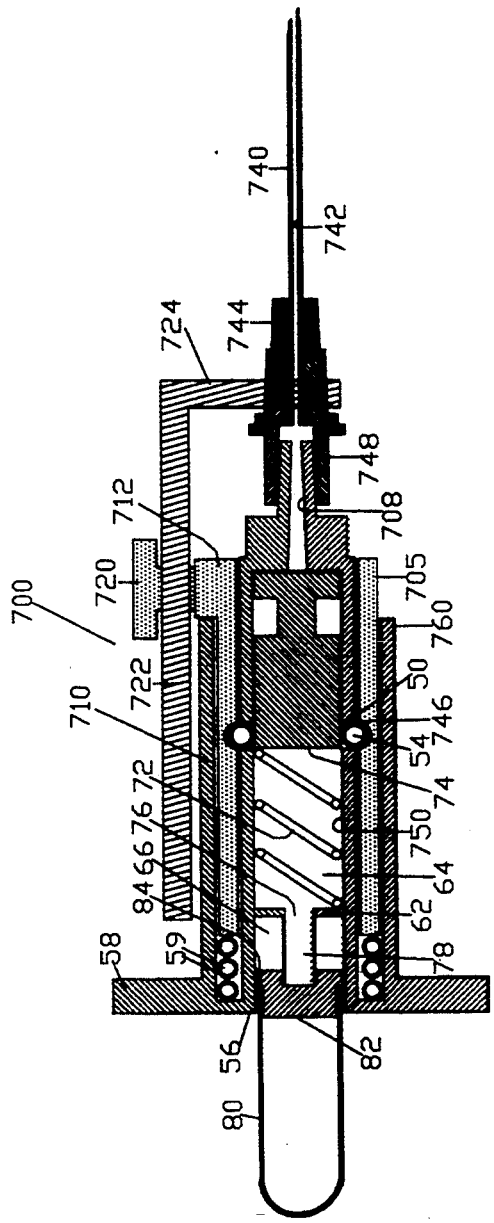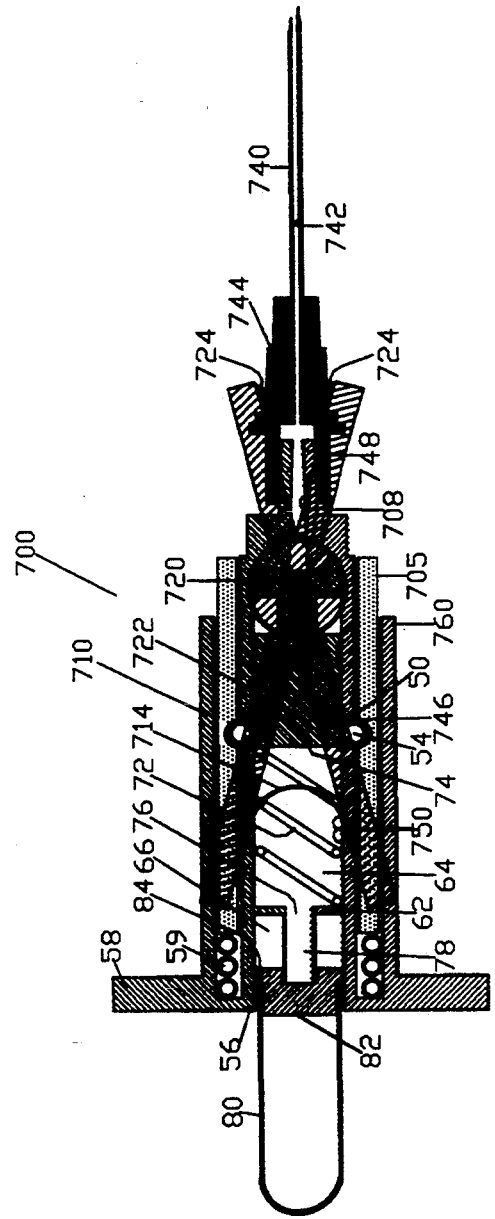

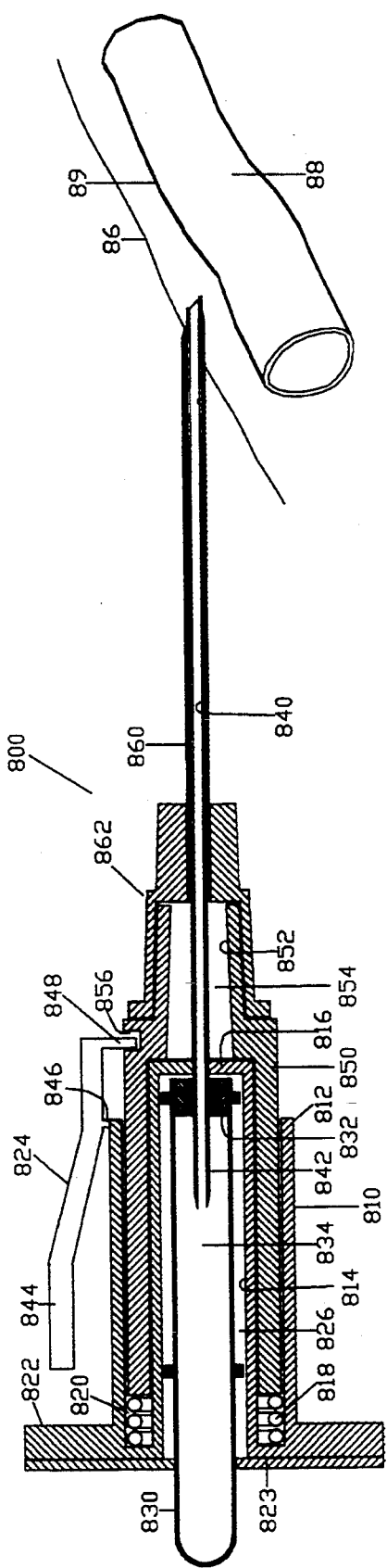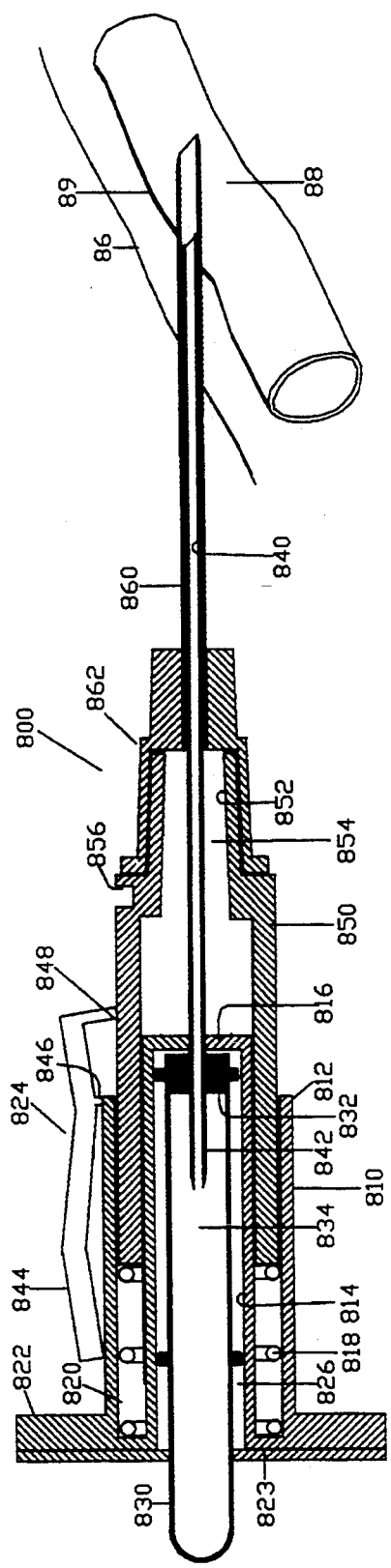

AUTOMATIC CANNULATION DEVICE

This is a continuation in part of Ser. No. 07/834,161 filed Feb. 11, 1992 now abandoned, which is a continuation in part of Ser. No. 07/759,159 filed Sep. 13, 1991 now abandoned.

BACKGROUND

1. Technical Field

This invention relates to blood vessel cannulation devices and is particularly directed to automatic means for catheter placement within blood vessels.

2. Background Art

Cannulating blood vessels is a common procedure in patient care, in order to administer fluids, drugs, blood or blood products. Heretofore, there have been two basic types of catheter for accomplishing cannulation. In one instance, the needle is within the catheter; while in the other instance, the catheter is within the needle. In both cases, the needle serves to penetrate the skin and the wall of the blood vessel and, once the blood vessel has been entered, the catheter is advanced manually until an adequate position is reached. Unfortunately, such manual catheter placement involves both of the operator's hands; one for stabilization of the needle, and the other for advancement of the catheter. Furthermore, manual catheter placement is an extremely delicate procedure which can be performed only by specially trained and highly skilled medical personnel and, even then, placement failure is not uncommon, due to such factors as failure to recognize penetration of the blood vessel, sequence delays, disruption of the continuity of the blood vessel, patient anatomical variability, etc.

A search in the United States Patent Office has revealed the following references:

| U.S. Pat. No. | INVENTOR | ISSUED |
| --- | --- | --- |
| 4,767,407 | S. J. Foran | Aug. 30, 1988 |
| 4,904,240 | R. L. Hoover | Feb. 27, 1990 |
| 4,944,728 | M. W. Carrell et al | Jul. 31, 1990 |
| 4,966,589 | J. M. Kaufman | Oct. 30, 1990 |

Each of these references requires manual advancement of the catheter and, hence, is subject to the disadvantages discussed above. Thus, none of the prior art catheter placement devices has been entirely satisfactory.

BRIEF SUMMARY AND OBJECTS OF INVENTION

These disadvantages of prior art catheter placement devices are overcome with the present invention and an improved catheter placement device is proposed which automatically advances the catheter, once the blood vessel has been penetrated, and which may be triggered one-handedly or, in a preferred embodiment, includes means for sensing penetration of a blood vessel and for automatically advancing the catheter in response to such penetration.

The advantages of the present invention are preferably attained by providing an improved catheter placement device comprising a needle, a catheter concentric with the needle, resilient means urging said catheter to an advanced position, and means for triggering the resilient means upon penetration of the wall of a blood vessel. The triggering means may be manual or may include means for sensing penetration of a blood vessel and for automatically advancing the catheter in response to such penetration.

Accordingly, it is an object of the present invention to provide an improved catheter placement device.

Another object of the present invention is to provide an improved catheter placement device which permits onehanded insertion and placement of a catheter.

An additional object of the present invention is to provide an improved catheter placement device which permits automatic advancement of the catheter, once a blood vessel has been penetrated.

A specific object of the present invention is to provide an improved catheter placement device comprising a needle, a catheter concentric with the needle, self-propelled, automatic means for catheter advancement, and means for triggering said means for self-propelled advancement upon penetration of the wall of a blood vessel. The triggering means may be manual or may include means for sensing penetration of a blood vessel and for automatically advancing the catheter in response to such penetration.

These and other objects and features of the present invention will be apparent from the following detailed description, taken with reference to the figures of the accompanying drawings.

BRIEF DESCRIPTION OF THE DRAWING

FIG. 1 is a transverse section through a catheter placement device embodying the present invention;

FIG. 2 is a view, similar to that of FIG. 1, showing the catheter placement device is its unlocked position;

FIG. 3 is a vertical section through the catheter placement device of FIG. 1, taken on the line 44 of FIG. 1;

FIG. 4 is a plan view of the latch member of the catheter placement device of FIG. 1;

FIG. 9 is transverse section through another alternative form of the catheter placement device of FIG. 1, shown in its unarmed condition;

FIG. 10 is a view showing the catheter placement device of FIG. 9 in its armed condition, after penetration of the skin, but prior to penetration of a blood vessel;

FIG. 11 is a view showing the catheter placement device of FIG. 9 immediately after penetration of a blood vessel;

FIG. 12 is a view showing the catheter placement device of FIG. 9 following advancement of the catheter;

FIG. 15 is a view showing the catheter placement device of FIG. 13 in its armed condition, after penetration of the skin, but prior to penetration of a blood vessel;

FIG. 16 is a view showing the catheter placement device of FIG. 13 following advancement of the catheter;

FIG. 17 is a view, similar to that of FIG. 1, showing another alternative form of the catheter placement device of FIG. 1;

FIG. 20 is a view, similar to FIG. 9, showing a further alternative form of the catheter placement device of FIG. 9;

FIG. 21 is a view, similar to that of FIG. 20, showing the catheter placement device of FIG. 20 in its "armed" position;

FIG. 22 is a view, similar to that of FIG. 9, showing another alternative form of the catheter placement device of FIG. 9;

FIG. 23 is a view, similar to that of FIG. 22 showing the catheter placement device of FIG. 21 in its "armed" position;

FIG. 24 is a view, similar to that of FIG. 22 showing the catheter placement device of FIG. 22 immediately after penetration of a blood vessel;

FIG. 25 is a view, similar to that of FIG. 22 showing the catheter placement device of FIG. 22 immediately after release of the catheter;

FIG. 29 is a view, similar to that of FIG. 27, showing the catheter placement device of FIG. 27 after skin penetration and the beginning of the automatic arming process;

FIG. 30 is a view, similar to that of FIG. 27, showing the catheter placement device of FIG. 27 after skin penetration, in a further stage of the arming process;

FIG. 31 is a view, similar to that of FIG. 27, showing the catheter placement device of FIG. 27 immediately after penetration of a blood vessel;

FIG. 32 is a view, similar to that of FIG. 27, showing the catheter placement device of FIG. 27 immediately after release of the catheter;

FIG. 33 is a view, similar to that of FIG. 27, after the removal of the needle, showing connection of the catheter with the intravenous tubing;

FIG. 35 is a view, similar to that of FIG. 34, showing the catheter placement device of FIG. 34 immediately after skin penetration;

FIG. 36 is a view, similar to that of FIG. 34, showing the catheter placement device of FIG. 34, immediately after release of the catheter;

FIG. 38 is a view, similar to that of FIG. 5, showing an alternative form of the catheter placement device of FIG. 5 prior to skin penetration;

FIG. 39 is a view, similar to that of FIG. 38, showing the catheter placement device of FIG. 38 immediately after skin penetration;

FIG. 48 shows an alternative form of the catheter placement device of FIG. 5;

FIG. 49 shows a top view of the same catheter device of FIG. 48;

FIG. 51 shows an alternative form of a semi-automatic catheter placement device;

FIG. 52 shows the catheter placement device of FIG. 51 after blood vessel penetration.

DETAILED DESCRIPTION OF THE INVENTION

Figure 5:
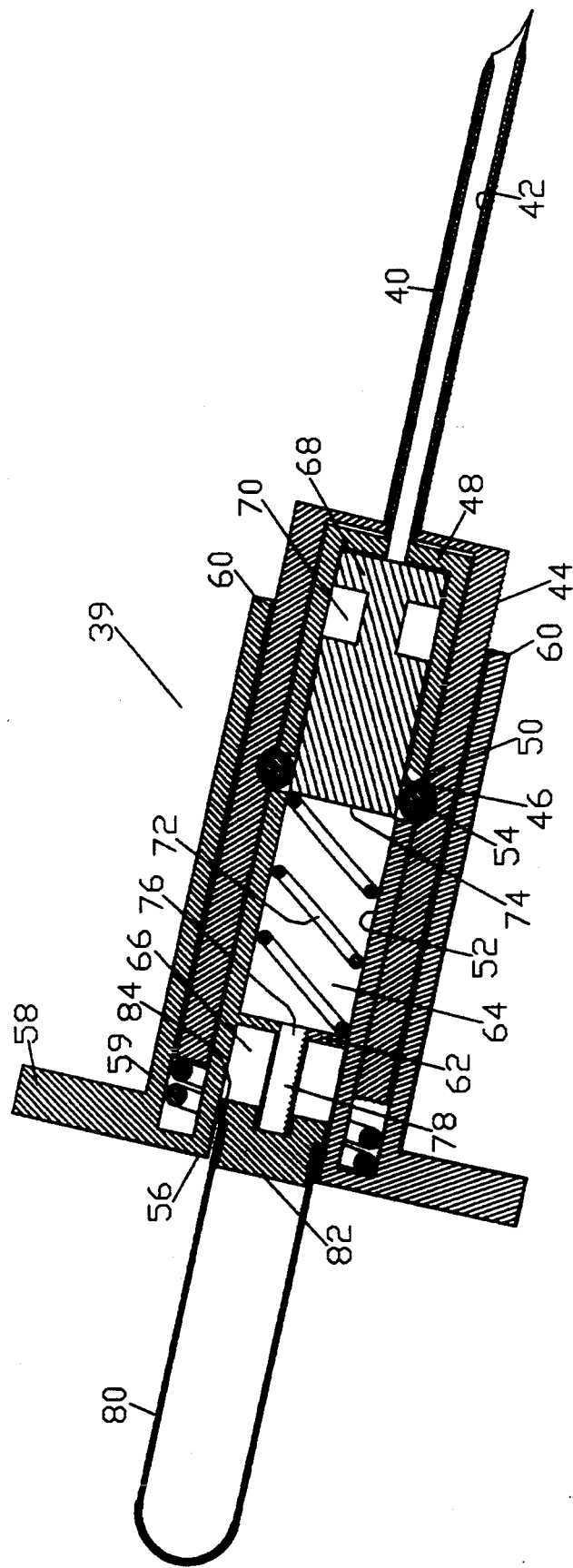
FIG. 5 is a transverse section through an alternative form of the catheter placement device of FIG. 1, shown in the unarmed condition.

In that form of the present invention chosen for purposes of illustration in FIG. 1, a catheter placement device, indicated generally at 10, is shown comprising a needle 12, having a tubular hollow shaft 14 projecting from a handle portion or needle hub 16, and a flexible catheter 18 projecting from a hub 20. As shown, the catheter 18 concentrically encircles the shaft 14 of the needle 12, while the catheter hub 20 telescopes over the forward portion of the needle handle portion 16. However, it will be apparent to those skilled in the art that, if desired, the needle 12 may be made to concentrically telescope over the catheter 18. The catheter hub 20 has a radial flange 22 formed adjacent the rear end 24 of the hub 20 and has a lever 26, formed of resilient material, projecting rearwardly from one side of the flange 22 and having an opening 28 formed adjacent the free end of the lever 26, as best seen in FIG. 4. A bridge member 30 projects radially outward from the needle handle 16 and, as best seen in FIG. 3, has an aperture 32 formed therein to receive the lever 26 and has a stud 34 projecting into the aperture 32 which is mateable with the opening 28 of the lever 26 to releasably retain the lever 26 and, hence, the hub 20 and catheter 18 in the position shown in FIG. 1. Finally, resilient means, such a spring 36, is mounted between the rear end 24 of the catheter hub 20 and the front end 38 of the handle portion 16 of the needle 12 to urge the hub 20 and catheter 18 forwardly.

In use, the catheter 18 and needle 12 are in the positions seen in FIG. 1, with the catheter 18 encircling the shaft 14 of the needle 12 and with opening 28 of lever 26 of the catheter 18 engaging the stud 34 of the bridge member 30 on the handle portion 16 of the needle 12 to releasably lock the catheter 18 in the position shown in FIG. 1. When the shaft 14 of the needle 12 penetrates a desired blood vessel, the operator presses the lever 26 toward the handle portion 16 of the needle 12, causing opening 28 of the lever 26 to disengage from the stud 34 and allowing spring 36 to drive the catheter 18 forwardly and, thereby, to advance and position the catheter 18 within the blood vessel. Thereafter, the needle 12 may be removed and the tubing containing the food, drugs or other desired material may be attached to the hub 20 of the catheter 18 for delivery of the desired material into the patient's blood vessel. It will be apparent that the lever 26 can be operated by the same hand which is holding the needle handle 16, thus, enabling the operator to position the needle 12, advance and place the catheter 18 and withdraw the needle 12 in a one-handed operation, leaving the operator's other hand free for other purposes.

Figure 6:
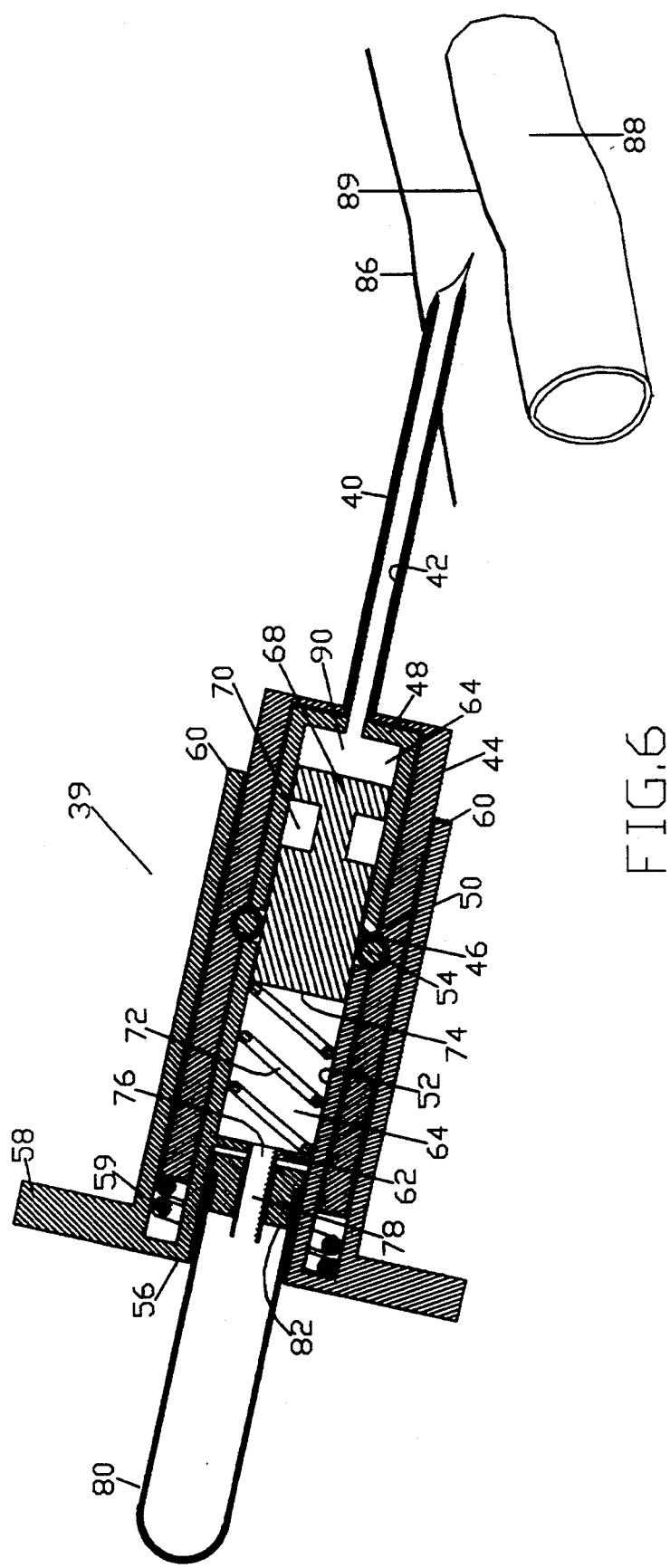
FIG. 6 is a view showing the catheter placement device of FIG. 5 in its armed condition, after penetration of the skin, but prior to penetration of a blood vessel.
Figure 7:
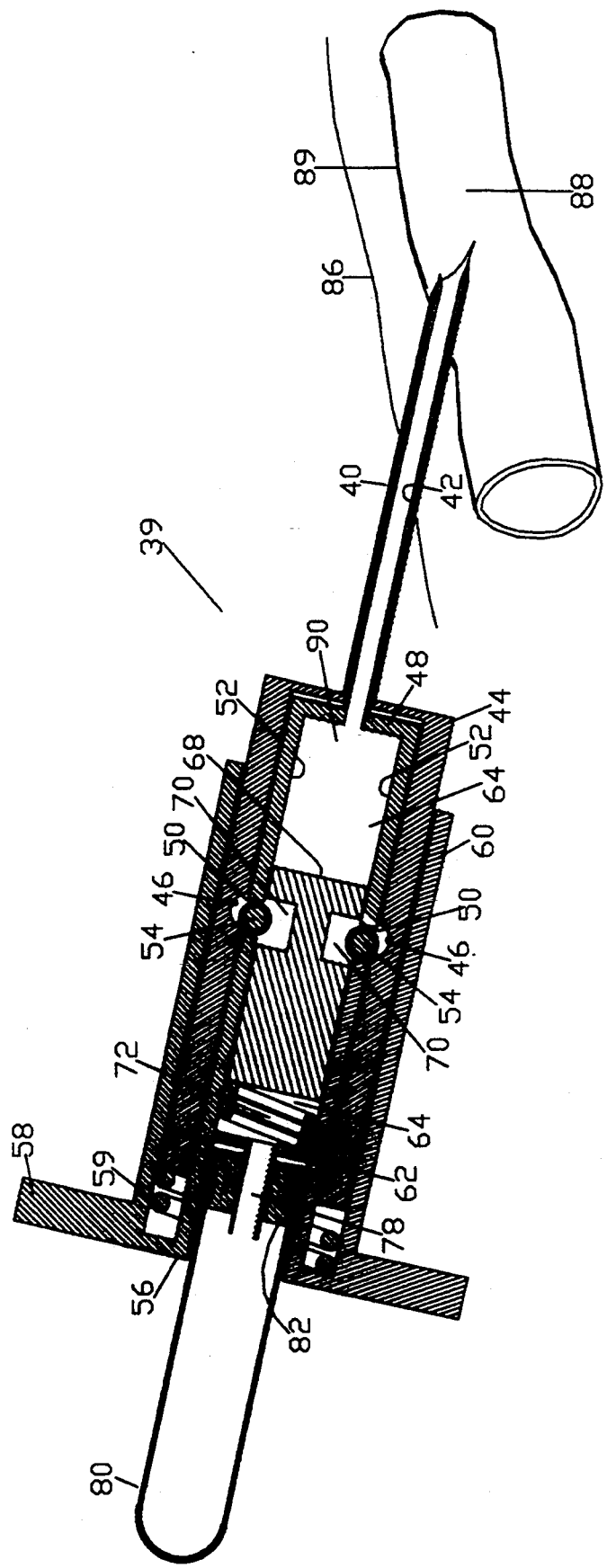
FIG. 7 is a view showing the catheter placement device of FIG. 5 immediately following penetration of a blood vessel.
Figure 8:
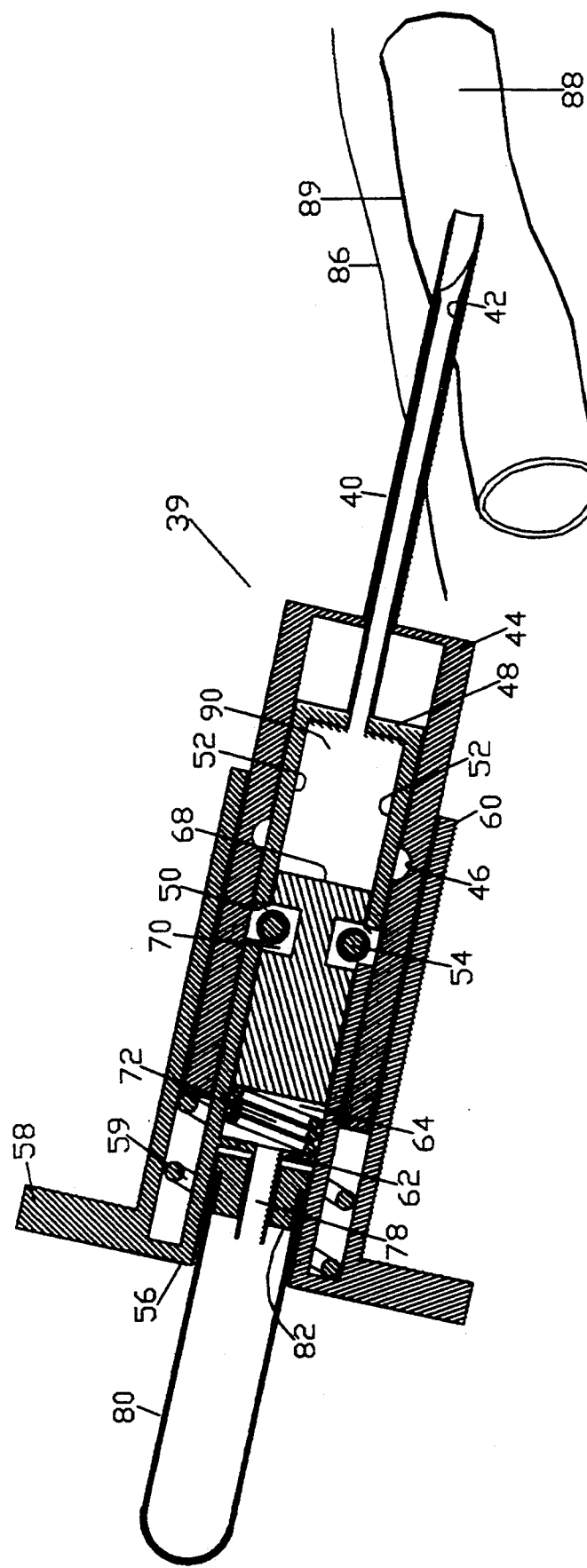
FIG. 8 is a view showing the catheter placement device of FIG. 5 following advancement of the catheter.

FIGS. 5–8 show an alternative form, indicated generally at 39, of the catheter placement device 10 of FIG. 1 which serves to automatically advance the catheter when the blood vessel is penetrated. In this form of the present invention, the catheter 40 encircles the needle shaft 42 and has a hub 44 formed with an annular recess 46 extending about the interior surface of the hub 44. The needle 42 has a generally cylindrical hub 48 formed with openings 50 in the side walls 52 of the needle hub 48 to receive balls 54, to releasably lock the catheter hub 44 in the position shown in FIG. 5, as will be more fully explained hereafter. The rear end 56 of the needle hub 48 carries a radial flange 58 and a cylindrical wall 60 extends forwardly from the flange 58 to encircle and guide movement of the catheter hub 44, which is telescopically slideably between the needle hub 48 and the cylindrical wall 60. A spring 59 is mounted within the cylindrical wall 60 rearwardly of the catheter hub 44 and serves to urge the catheter hub 44, and consequently, the catheter 40 forwardly. A wall member 62 divides the interior of the needle hub 48 and defines a forward vacuum chamber 64 and a rearwardly opening recess 66. Within the forward chamber 64, a piston 68 is slideably mounted and has an annular recess 70 extending about the periphery of the piston 68, which serves to receive the balls 54 when the catheter 40 is released, as hereinafter described. A spring 72 is located between the wall member 62 and the piston 68 to normally urge the piston 68 to seat against the forward end of the chamber 64, as seen in FIG. 5, so that the body 74 of the piston 68 serves to force the balls 54 to extend through openings 50 to engage the recess 46 of the catheter hub 44 and, hence, to releasably lock the catheter hub 44 in the position shown in FIG. 5, against the urging of spring 59. The wall member 62 has a central opening 76 and a post-needle member 78 is mounted in the opening 76 and projects rearwardly as shown. A capsule 80 is slideably mountable within the rearwardly opening recess 66 of the needle hub 48 and has a plug 82 closing the open end 84 of the capsule 80. The capsule 80 contains a vacuum and the plug 82 is rupturable, when pressed against the post-needle member 78, to cause partial retraction of the piston 68, as more fully described below. FIG. 5 shows the catheter placement device 39 in preparation for use, but prior to insertion. FIG. 6 shows the catheter placement device 39 after the needle 42 has penetrated the skin 86 of a patient, but prior to penetration of a blood vessel 88. Once the needle 42 has entered the skin 86, the operator presses the vacuum capsule 80 forwardly, causing the post-needle member 78 to pierce the plug 82. This causes air from the forward chamber 64 of the needle hub 48 to enter the capsule 80, which creates a partial vacuum within the chamber 64 and serves to partially retract piston 68 against the action of spring 72. This, in turn, creates a vacuum within the chamber 64 forwardly of the piston 68, as seen at region 90. However, the body 74 of the piston 68 still serves to force the balls 54 into recess 46 to continue locking the catheter hub 44 in its retracted position, as seen in FIGS. 5 and 6. The catheter placement device 39 is now "armed" to automatically advance the catheter 40. In FIG. 7, the needle 42 has penetrated the wall 89 of the patient's blood vessel 88. The instant that such penetration occurs, blood from the blood vessel 88 is drawn into region 90 by the vacuum in the region 90. This backflow of blood drives the piston 68 rearwardly, against the action of spring 72, to the point that the annular recess 70 of the piston 68 becomes aligned with openings 50 of the side walls 52 of the needle hub 48. Consequently, balls 54 can move into the recess 70 of the piston 68 and out of the recess 46 of the catheter hub 44. When this occurs, spring 59 drives the catheter hub 44 and catheter 40 forwardly, automatically, without any action by the operator, to advance and place the catheter 40, as seen in FIG. 8.

In use, the catheter placement device 39 is initially in the position shown in FIG. 5, with the catheter 40 retracted and with piston 68 urged forwardly by spring 72, causing balls 54 to pass through openings 50 in the side walls 52 of the needle hub 48 to enter recess 46 of the catheter hub 44 and, hence, to lock the catheter 40 in its retracted position. Once the operator has inserted the needle 42 into the skin 86 of the patient, the operator presses the vacuum capsule 80 forward, causing the post-needle member 78 to penetrate the plug 82. This causes air from chamber 64 of the needle hub 48 to enter the vacuum capsule 80 and serves to partially retract the piston 68 to create a vacuum within region 90 forward of the piston 68, as seen in FIG. 6, and thereby "arming" the catheter placement device 39. Subsequently, the instant the needle 42 penetrates the patient's blood vessel 88, as seen in FIG. 7, blood from the blood vessel 88 is drawn into region 90 of the needle hub chamber 64. This drives the piston 68 rearwardly, against the action of spring 72, until annular recess 70 of the piston 68 becomes aligned with openings 50 in the side walls 52 of the needle hub 48, which allows balls 54 to move out of recess 46 of the catheter hub 44. This automatically unlocks the catheter hub 44 and allows spring 59 to advance the catheter 40, as seen in FIG. 8. Because the advancement of the catheter 40 occurs automatically and instantly, in response to penetration of the blood vessel 88 by the needle 42, proper placement of the catheter 40 is assured and overpenetration or underpenetration are avoided. Furthermore, pressing of the vacuum capsule 80 against the post-needle member 78, to "arm" the catheter placement device 39, can be accomplished by the operator as a one-handed operation. Thus, the catheter placement device 39 provides simple and automatic, yet highly accurate placement of the catheter 40.

FIGS. 9–12 show another alternative form, indicated generally at 92, of the catheter placement device 10 of FIG. 1 comprising a needle shaft 94 projecting from a generally cylindrical hub 96 having a flange 98 extending radially outward from the rear end 100 of the needle hub 96 and having a cylindrical sleeve 102 extending forwardly from the flange 98 and spaced from the side wall 103 of the cylindrical hub 96 to define a space 104 therebetween. A flexible tubular catheter 106 encircles the needle shaft 94 and projects forwardly from a generally cup-shaped catheter hub 108 having a side wall 110 which is telescopically slideable within the space 104 of the needle hub 96. A spring 112 is positioned within the space 104 between the flange 98 of the needle hub 96 and the rear end of the side wall 110 of the catheter hub 108 and serves as a self-propelling means to urge the catheter hub 108 forwardly. The side wall 110 of the catheter hub 108 is formed with an internal annular recess 114 and the side wall 103 of the cylindrical needle hub 96 are formed with openings 116 and balls 118 are seated in the openings 116 and extend into the recess 114 to releasably lock the catheter hub 108 in its retracted position and in turn actuate the self-propelling means 112, as seen in FIGS. 9, 10 and 11. A piston 120 is slideably mounted within vacuum chamber 148 delimited by the cylindrical needle hub 96 and is formed with an annular recess 122, located adjacent the forward end of the piston 120, and an axial recess 124, extending forwardly from the rear end 125 of the piston 120. The needle hub 96 has a stud 126 projecting radially outward adjacent the rear end 100 of the needle hub 96 and a trigger member 128 encircles the stud 126 and is slideably mounted thereon. The trigger member or arming means 128 is formed with a pair of forwardly projecting flanges 130 and 132. Flange 130 extends forwardly from the inner edge 134 of the rear surface 136 of the trigger member 128 and a spring 127 is seated between the stud 126 and the trigger member 128 to urge the trigger member outward causing flange 130 of the trigger member 128 to normally engage the rear end 125 of the piston 120, as seen in FIG. 9, and serving to normally prevent rearward movement of the piston 120. Flange 132 extends forwardly from the inner edge 138 of the front surface 140 of the trigger member 128. A latch member 142 is supported by a resilient stem 143, which projects outwardly from the outer surface of the sleeve 102 of the needle hub 96 adjacent flange 132 of the trigger member 128. The latch member 142 has an inclined rear surface 144, which is normally positioned to partially underlie the end of flange 132 of the trigger member 128, as seen in FIG. 9. Finally, a spring 146 is located within the cylindrical needle hub 96 forwardly of the piston 120 to normally urge the piston 120 rearwardly.

In use, the catheter placement device 92 is normally in the condition seen in FIG. 9 with the trigger member 128 urged outwardly by spring 127 urging trigger member 128 to its outward position wherein flange 130 engages piston 120 to hold the piston 120 in its forward position compressing spring 146 and forcing balls 118 through openings 116 of the needle hub 96 into recess 114 of the catheter hub 108 to releasably lock the catheter hub 108 in its retracted position. Once the operator has caused the needle shaft 94 to penetrate the patient's skin 86, as seen in FIG. 10, the operator presses the trigger member 128 inward toward the cylindrical sleeve 102 of the needle hub 96, causing flange 130 of the trigger member 128 to disengage from piston 120 and to enter the axial recess 124 of the piston 120, which allows spring 146 to drive the piston 120 slightly rearward, as seen in FIG. 10, and creating a vacuum in the chamber 148 forward of the piston 120 within the cylindrical needle hub 96. At the same time, flange 132 of the trigger member 128 moves inwardly past the inclined surface 144 of the latch member 142, causing the latch member 142 to cam forwardly on the resilient stem 143. When flange 132 has past the inclined surface 144, the resilient stem 143 returns the latch member 142 to its original position, in which it now overlies flange 132 to lock the trigger member 128 in its "armed" position, as seen in FIGS. 10, 11 and 12. When the operator causes the needle shaft 94 to penetrate the wall 89 of a blood vessel 88, blood from the blood vessel is instantly drawn into the space 148 within the needle hub 96, due to the vacuum created therein when spring 146 drove the piston 120 to its partially retracted position, as seen in FIG. 10. The vanishing of the vacuum due to entering or backflow of the blood in the space 148 forces the piston 120 to its fully retracted position, as seen in FIG. 11, which causes the annular recess 122 of the piston 120 to become aligned with openings 116 of side wall 103 of the needle hub 96 and allowing balls 118 to move out of the annular recess 114 of the side wall 110 of the catheter hub 108. This unlocks the catheter hub 108 and actuates the spring or self-propelling means 112 to drive the catheter hub 108 forward to advance and place the catheter 106, as seen in FIG. 12. Again, it will be apparent that the operator can use one hand to grasp and position the catheter placement device 92, during insertion of the needle 94 into the patient's skin 86 and to actuate the trigger member 128 to "arm" the catheter placement device 92 prior to penetration of the blood vessel 88, so that the catheter placement device 92 can instantly and automatically advance and place the catheter 106 upon penetration of the blood vessel 88, without additional effort by the operator.

Figure 13:
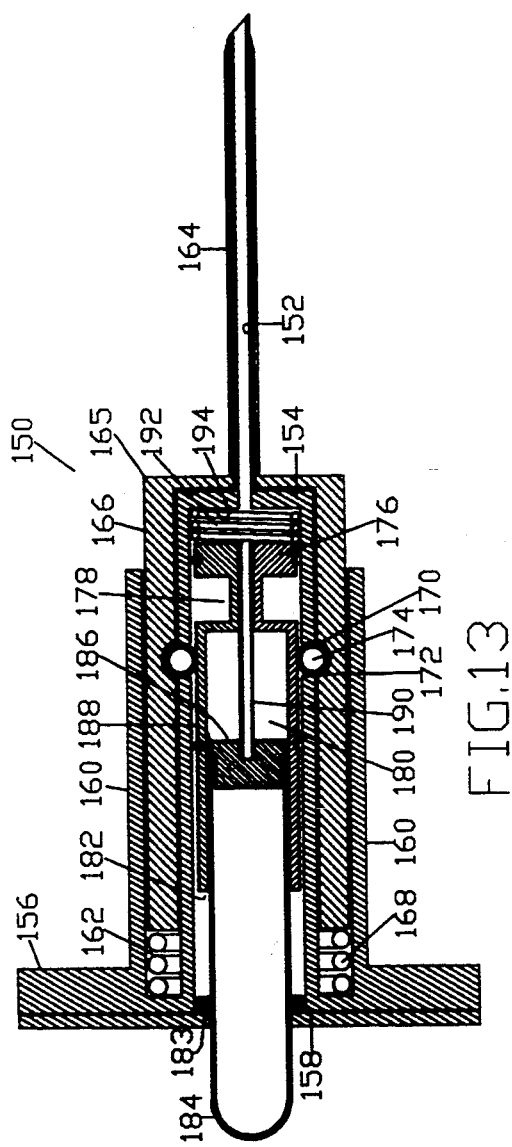
FIG. 13 is a transverse section through a further alternative form of the catheter placement device of FIG. 1, shown in its unarmed condition.
Figure 14:
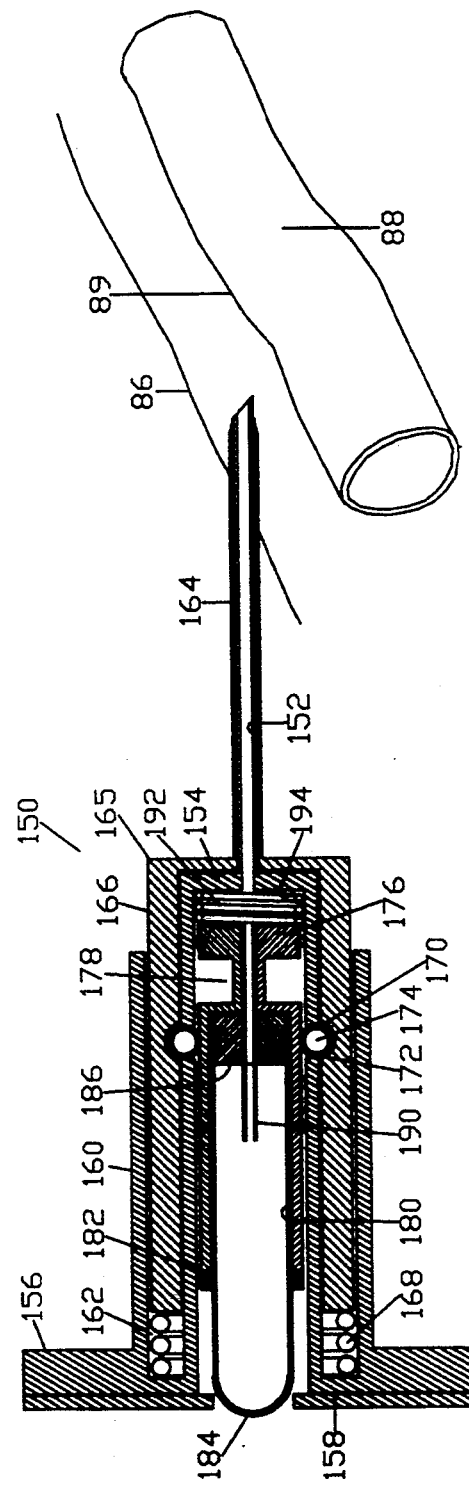
FIG. 14 is a view showing the catheter placement device of FIG. 13 in its armed condition, after penetration of the skin, but prior to penetration of a blood vessel.

FIGS. 13–16 show another alternative form, indicated generally at 150, of the catheter placement device 10 of FIG. 1 comprising a needle shaft 152 projecting from a generally cylindrical hub 154 having a flange 156 extending radially outward from the rear end 158 of the needle hub 154 and having a cylindrical sleeve 160 extending forwardly from the flange 156 and spaced from the cylindrical hub 154 to define a space 162 therebetween. A flexible tubular catheter 164 encircles the needle shaft 152 and projects forwardly from a generally cup-shaped catheter hub 165 having a side wall 166 which is telescopically slideable within the space 162 of the needle hub 154. A spring 168 is positioned within the space 162 between the flange 156 of the needle hub 154 and the rear end of the side wall 166 of the catheter hub 165 and serves to urge the catheter hub 165 forwardly. The side wall 166 of the catheter hub 165 is formed with an internal annular recess 170 and the cylindrical needle hub 154 is formed with openings 172 and balls 174 are seated in the openings 172 and extend into the recess 170 to releasably lock the catheter hub 165 in its retracted position, as seen in FIGS. 13 and 14. A piston 176 is slideably mounted within the cylindrical needle hub 154 and is formed with an annular recess 178, located adjacent the forward end of the piston 176, and a rearwardly-opening recess 180, extending forwardly from the rear end 182 of the piston 176. A generally U-shaped capsule 184 is slideably mountable within the rearwardly-opening recess 180 of the piston 176 and has a plug 186 closing the open end 188 of the capsule 184. The capsule 184 contains a vacuum and the plug 186 is rupturable, when pressed against a post-needle member 190 carried by the piston 176 and projecting rearwardly therefrom, to create a vacuum within the space 194 which "arms" the catheter placement device 150.

When the operator has inserted the needle shaft 152 into the skin of the patient, the operator presses the vacuum capsule 184 inward to cause the post-needle member 190 to pierce the plug 186 to "arm" the catheter placement device 150. Subsequently, the instant the needle 152 penetrates the wall 89 of the blood vessel 88, the vacuum in the space 194 causes blood to backflow into the space 194 and the vanishing of the vacuum due to the blood entering the space 194 drives the piston 176 to its fully retracted position, as seen in FIG. 15, wherein the annular recess 178 of the piston 176 is aligned with openings 172 in the side wall of the needle hub 154, which allows the balls 174 to move out of the annular recess 170 in the side wall 166 of the catheter hub 165. This "unlocks" the catheter hub 165 and actuates spring 168 to drive the catheter hub 165 forward to advance and place the catheter 164 within the blood vessel 88, as seen in FIG. 16. Here, again, the operator can use one hand to insert the needle 152 into the patient's skin 86 and to press the vacuum capsule 184 inward to "arm" the catheter placement device 150. Subsequently, upon penetration of a blood vessel 88, the catheter placement device 150 will, instantly and automatically, advance and place the catheter 164 without any additional action by the operator.

FIG. 17 shows an alternative form, indicated generally at 196, of the catheter placement device 10 of FIG. 1. The catheter placement device 196 is substantially identical with that of the catheter placement device 10 of FIG. 1, except that the spring 36 of the catheter placement device 10 is replaced by a pair of magnets 198 and 200 as a self-propelling means mounted with like poles in opposing relation, as indicated by arrows 202. In this way, when lever 26 is released, the magnets 198 and 200 will serve to drive the catheter hub 20 away from the front end 38 of the needle 12 and, hence, will serve to automatically advance the catheter 18.

Figure 18:
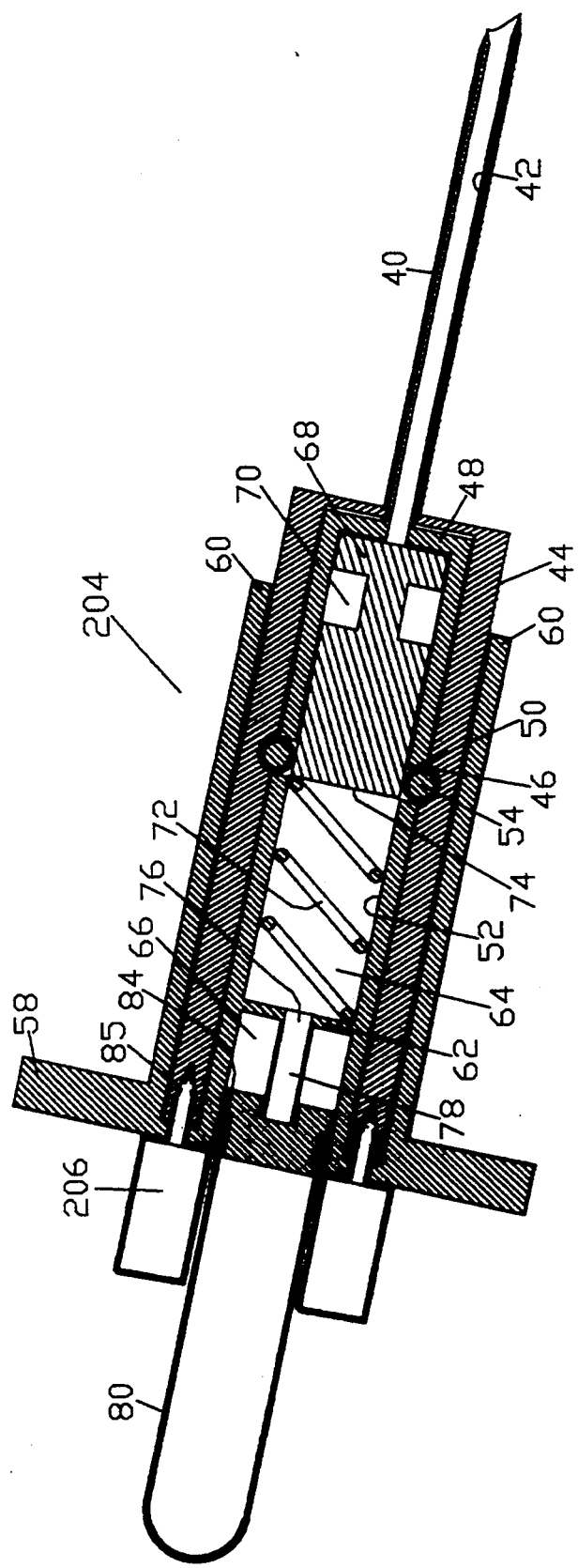
FIG. 18 is a view, similar to FIG. 5, showing another alternative form of the catheter placement device of FIG. 5.

FIG. 18 shows an alternative form, indicated generally at 204, of the catheter placement device 39 of FIG. 5. The catheter placement device 204 is substantially identical with that the catheter placement device 39 of FIG. 5, except that the spring 59 of the catheter placement device 39 is replaced by a quantity of compressed gas as a self-propelling means which is supplied from a suitable source, such as capsule 206.

In use, the catheter placement device 204 functions in substantially the same manner as the catheter placement device 39, except that when the catheter hub 44 is unlocked the catheter 40 is automatically advanced by expansion of the compressed gas from capsule 206, rather than by expansion of spring 59.

Figure 19:
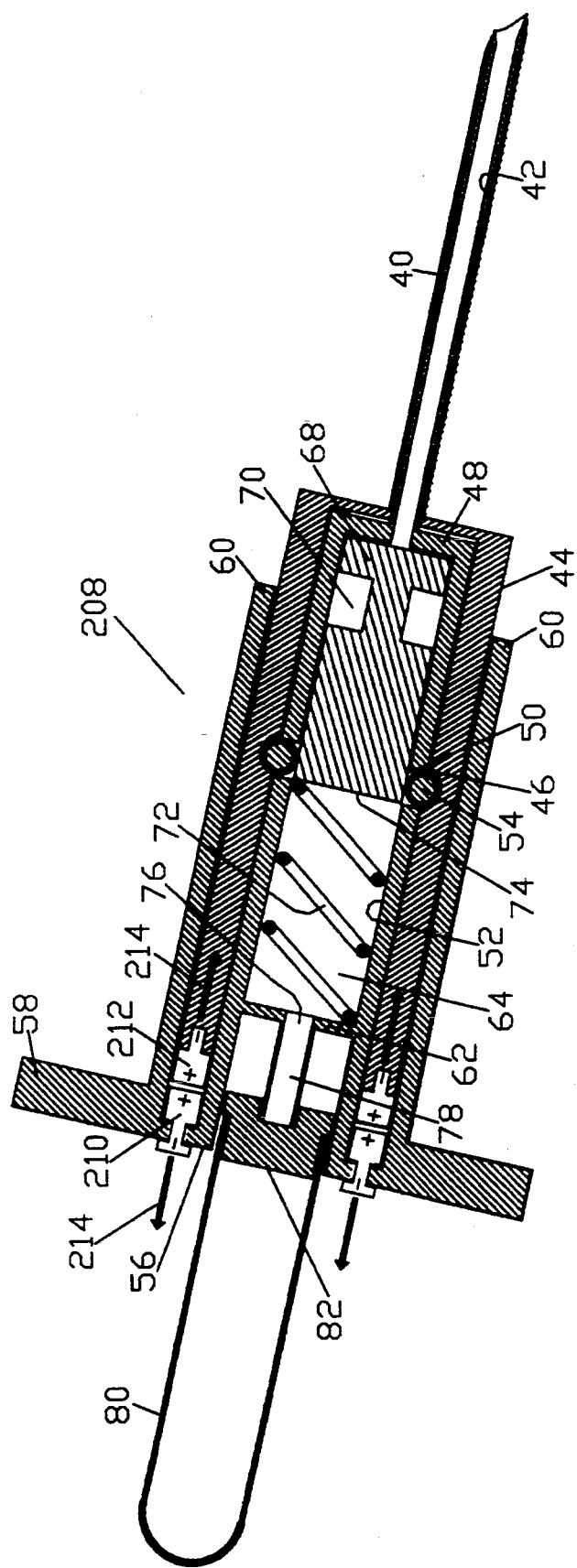
FIG. 19 is a view, similar to that of FIG. 5, showing an additional alternative form of the catheter placement device of FIG. 5.

FIG. 19 shows another alternative form, indicated generally at 208, of the catheter placement device 39 of FIG. 5. The catheter placement device 208 is substantially identical with that the catheter placement device 39 of FIG. 5, except that the spring 59 of the catheter placement device 39 is replaced by a pair of magnets 210 and 212 mounted with like poles in opposing relation, as indicated by arrows 214.

In use, the catheter placement device 208 functions in substantially the same manner as the catheter placement device 39, except that when the catheter hub 44 is unlocked, the magnets 210 and 212 will serve to automatically drive the catheter 40 forward for placement, rather than by expansion of spring 59.

FIGS. 20 and 21 show a further alternative form, indicated generally at 214, of the catheter placement device 92 of FIG. 9. The catheter placement device 214 is substantially identical with that of the catheter placement device 92 of FIG. 9, except that the locking balls 118, openings 116 and advancing spring 112 of the catheter placement device 92 of FIG. 9 have been omitted. Instead, a cylindrical chamber 216 is provided adjacent the rear end 100 of the needle hub, projecting inwardly from the side wall 103 of the needle hub 96. The cylinder 216 has an opening 218 facing toward the rear end 125 of the piston 120 and a piston 220 is slideably mounted in the opening 218. The rear end of the cylinder 216 is connected to a generally U-shaped duct 222 and a shaft 224 is carried by the rear end of the catheter hub 108 and projects into the end 226 of the duct 222. The cylinder 216 and duct 222 are filled with a suitable hydraulic fluid 228.

In use, when button 128 is pressed inwardly, it releases piston 120, which is driven partially rearward by spring 146. However, as the piston 120 moves rearwardly, it creates a vacuum within space 148 which prevents full rearward movement of the piston 120. Subsequently, penetration of a blood vessel allows blood to backflow into chamber 148 and the vanishing of the vacuum due to the entering of the blood into chamber 148 serves to drive the piston 120 rearward. The piston ring or sealing ring 240 assures that the vacuum in space 148 will be maintained. The vanishing of the vacuum due to the entering of the blood into space 148 drives piston 120 farther rearward, which allows piston ring 240 to expand out of recess 242 in expanded posterior portion of vacuum chamber 148 and enables spring 146 to drive piston 120 fully rearward causing the rear end 125 of piston 120 to engage piston 220 and to drive the piston 220 rearwardly within cylinder 216. This forces the hydraulic fluid 228 to flow through duct 222 and to drive shaft 228 forwardly to release the catheter hub 108.

FIGS. 22, 23, 24 and 25 show yet another alternative form, indicated generally at 230, of the catheter placement device 92 of FIG. 9. The catheter placement device 230 is substantially identical to the catheter placement device 92 of FIG. 9, except that the locking balls 118, openings 116 and advancing spring 112 of the catheter placement device 92 of FIG. 9 have been omitted and the advancing spring 112 is replaced by self-propelling means comprising a cam 232 which is pivotally mounted in the side wall 103 of the needle hub 102. The cam 232 has a trigger portion 234 and an actuator portion 236, which is engageable with the rear end 238 of the side wall 110 of the catheter hub 108. Finally, a piston ring 240 is mounted in a recess 242 of the piston 120 and frictionally engages the side wall 103 of vacuum chamber or space 148 of the needle hub 102.

In use, when, after skin penetration, the trigger button 128 is pressed, it moves arm 130 out of engagement with piston 120, which allows spring 146 to drive piston 120 partially rearward, to the position seen in FIG. 23. However, the movement of piston 120 creates a vacuum within space 148 which opposes the action of spring 146 and limits the rearward movement of the piston 120. The piston ring 240 assures that the vacuum in space 148 will be maintained. Subsequently, penetration of a blood vessel 88 by the needle 94, allows blood to flow into space 148, as seen in FIG. 24. The vanishing of the vacuum due to the entering of the blood into space 148 drives piston 120 farther rearward, which allows piston ring 240 to expand out of recess 242 and enables spring 146 to drive piston 120 fully rearward to engage the trigger portion 234 of cam 232, causing cam 232 to pivot and causing the actuator portion 236 of cam 232, as seen in FIG. 25 to drive the rear end 238 of side wall 110 of the catheter hub 108 forward to release and place the catheter 106.

Figure 26:
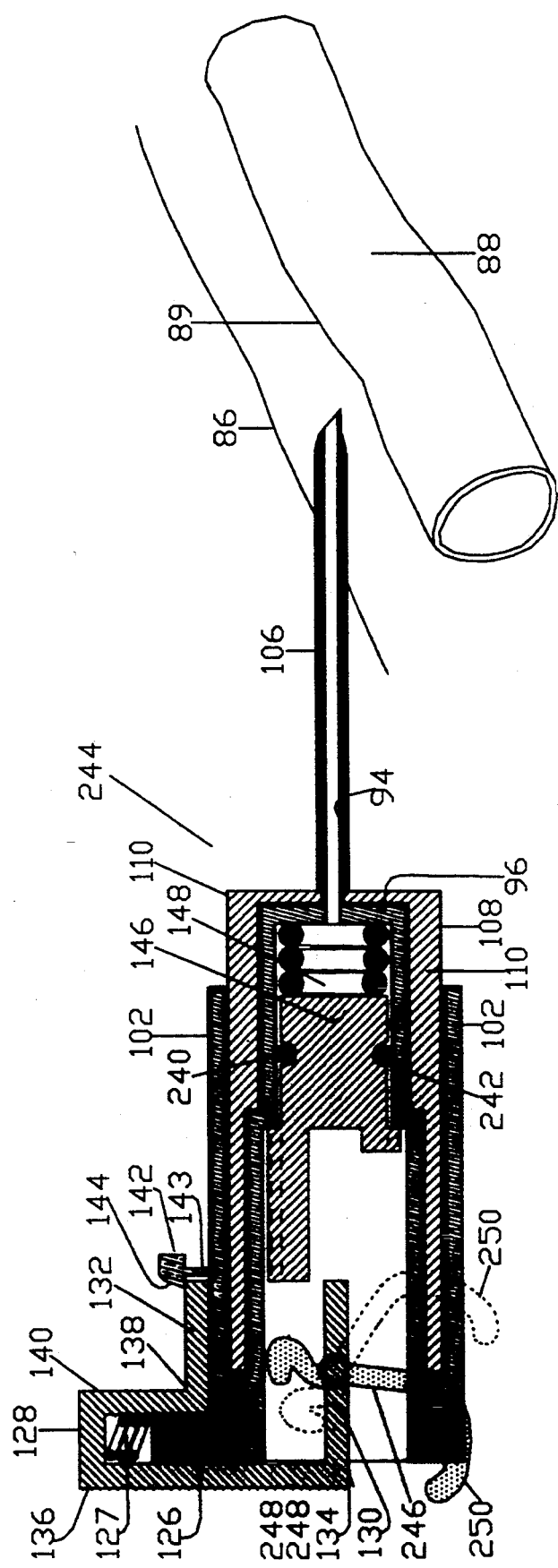
FIG. 26 is a view, similar to that of FIG. 9, showing an additional alternative form of the catheter placement device of FIG. 9.
Figure 27:
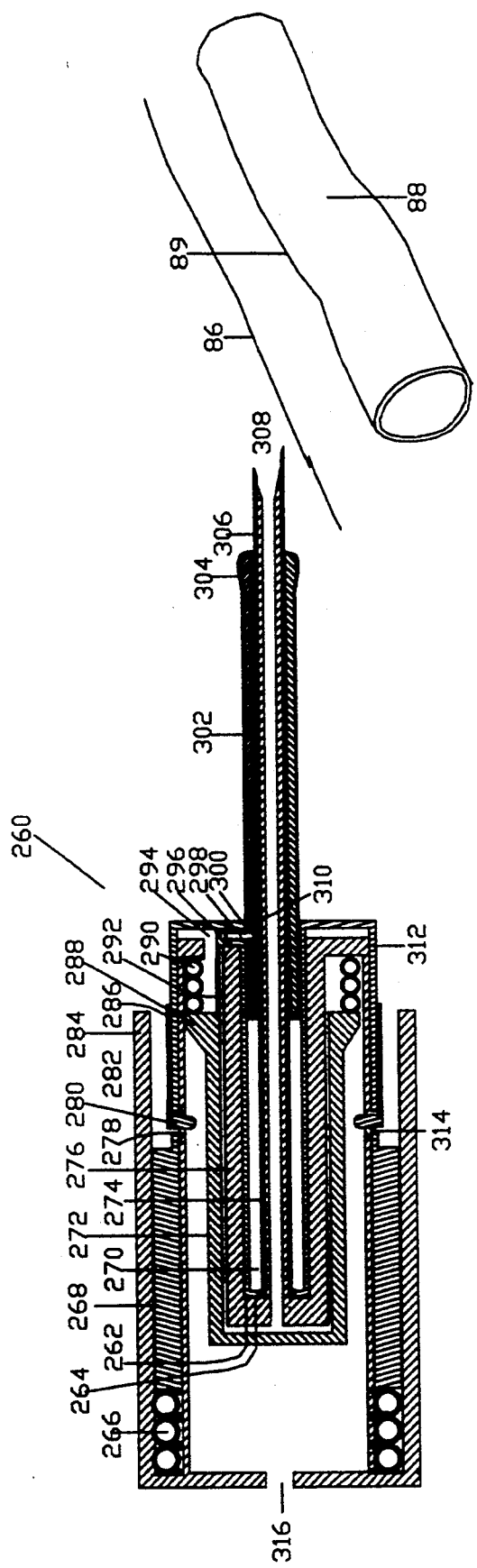
FIG. 27 shows an alternative form of the catheter placement device with an automatic arming rod.
Figure 28:
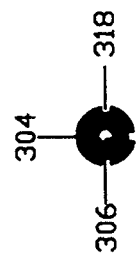
FIG. 28 shows a cross-section of the automatic arming rod of FIG. 27.

FIG. 26 shows yet another alternative form, indicated generally at 244, of the catheter placement device 230 of FIGS. 22, 23, 24 and 25. The catheter placement device 244 is substantially identical to the catheter placement device 230 of FIG. 22, except that the cam 232 is omitted and, instead, self-propelling means comprising a lever 246 is pivotally mounted on the forwardly extending arm 130 of the trigger button 128 and one side of the rearwardly extending portion 125 of piston 120 is omitted. The lever 246 comprises a trigger portion 248, which extends into the path of movement of the rearwardly extending portion 125 of piston 120, and an actuator portion 250 which engages the rear end 238 of the side wall 110 of the catheter hub 108.

In use, the catheter placement device 244 functions in substantially the same manner as the catheter placement device 230 of FIGS. 22, 23, 24 and 25. However, when the blood entering space 146 drives piston 120 rearwardly, the rearwardly extending position 125 of piston 120 engages the trigger portion 248 of the lever 246, causing the lever 246 to pivot, driving the trigger portion 248 rearwardly to the position seen in dotted lines in FIG. 26, and causing the actuator portion 250 of lever 246 to move forwardly, as seen in dotted lines in FIG. 26, to drive the rear end 238 of the catheter hub 108 forwardly to release and place the catheter 106.

FIGS. 27-33 show a fully automatic form of catheter placement device, indicated generally at 260, wherein the means for arming the sensing means which responds to blood vessel penetration is automatically actuable upon skin penetration by the needle. The catheter placement device 260 is essentially similar to the device of FIG. 9 with the following important differences: the arming means, which in FIG. 9 was represented by the trigger member 128, is represented in the device 260 by a cylinder or sleeve 302 surrounding the catheter and telescopically slideable on the catheter, of sufficient thickness, particularly in correspondence of its distal end 304 to not be permitted to follow the needle shaft 308 and catheter shaft 306 at the site of skin penetration, and to be retained as soon as the distal end of the cylinder is in contact with the skin. The retention of the cylinder, while the needle and catheter are being advanced inside the skin, will result in a backward movement of the cylinder relatively to the needle and the catheter. The backward movement of the cylinder will force the tooth 298 against a non-steep side of the notch 310 where the tooth was resting in its initial position, displacing it outward. In turn, the tooth 298 will force the resilient hook 296 outwardly causing the disengagement of the hollow piston 272, to which the resilient hook is anchored, from the edge 320 of a hole 294 formed in the front end of an anterior fold 322 of the needle hub connecting the internal needle hub 324 with the external needle hub 326. The piston 272, no longer retained, will be urged backward by the action of spring 290. However, the movement of piston 272 creates a vacuum within space or vacuum chamber 328 which opposes the action of spring 290 and limits the rearward movement of the piston. Subsequently, penetration of a blood vessel 88 by the needle 94 allows blood to flow into space 328, as seen in FIG. 31. The pressure of this blood drives piston 272 farther rearward, which allows flange 288 of piston 272 to outwardly displace the resilient hook 280, which is anchored to the catheter hub 312, out of the hole 278 formed in the external needle hub 326. Resilient hook 280 is the equivalent of the ball members of FIG. 9. The outward displacement of resilient hook 280 will result in a disengagement of the catheter hub 312, to which the hook 280 is anchored, from the needle hub 330. Such a disengagement will no longer retain the catheter hub 312 from the action of spring 266, and the catheter 306 will be propelled into an advanced position relatively to the needle. In FIG. 33, the catheter 306 is shown in its final intravenous position, after the removal of needle 308 and needle hub 284, connected to adaptor 260 of intravenous tubing 263.

Figure 34:
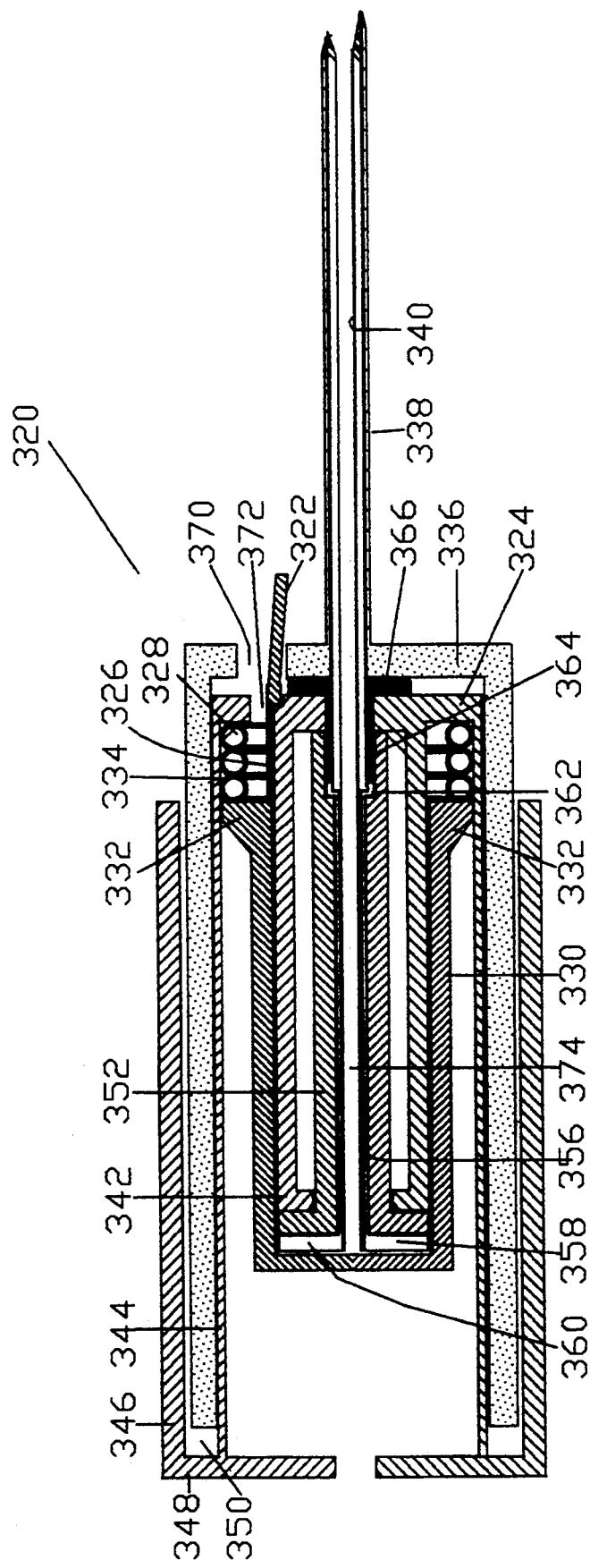
FIG. 34 shows an additional alternative form of the catheter placement device.

FIGS. 34-36 show another alternative form of a catheter placement device, indicated generally at 320. The catheter placement device 320 is essentially similar to the device of FIGS. 27-33 with the following important differences: the self-propelling catheter advancement is obtained by the expansion of expandable material 358 and the omission of catheter automatic arming. The needle hub 342 of the needle 340 contains a chamber 356 filled with a thermally expandable material 358, such as mercury. Chamber 356 has in its proximal portion a hollow piston 364 with flanges 366 interposed between the inner face of the catheter hub 336 and the front of the needle hub 324. A lever 322 with its resilient segment 326 attached to flange 332 of piston 330 protrudes through an opening 372 of catheter hub 336 and opening 370 of needle hub 342. This lever 322, in its resting position, locks hollow piston 330 in its advanced position, not allowing spring 328 to displace the piston 330 rearwardly. Once the tip of the needle 340 penetrates skin 86, the lever 322 is lifted by the operator, thus disengaging piston 330 to a rearward position, resulting in creation of a vacuum within the hollow needle shaft 340 and spaces 374 and 360. Upon penetration of needle 340 into a blood vessel 89, blood will rush into the spaces 374 and 360, via the hollow needle shaft 340. The blood, at 37 degrees Centigrades or warmer, will cause the thermally expandable material 358 to expand, provoking the rapid advancement of piston 364 which, acting upon catheter hub surfaces 336, will push forward, via its flanges, catheter 338 further inside blood vessel 89.

Figure 37:
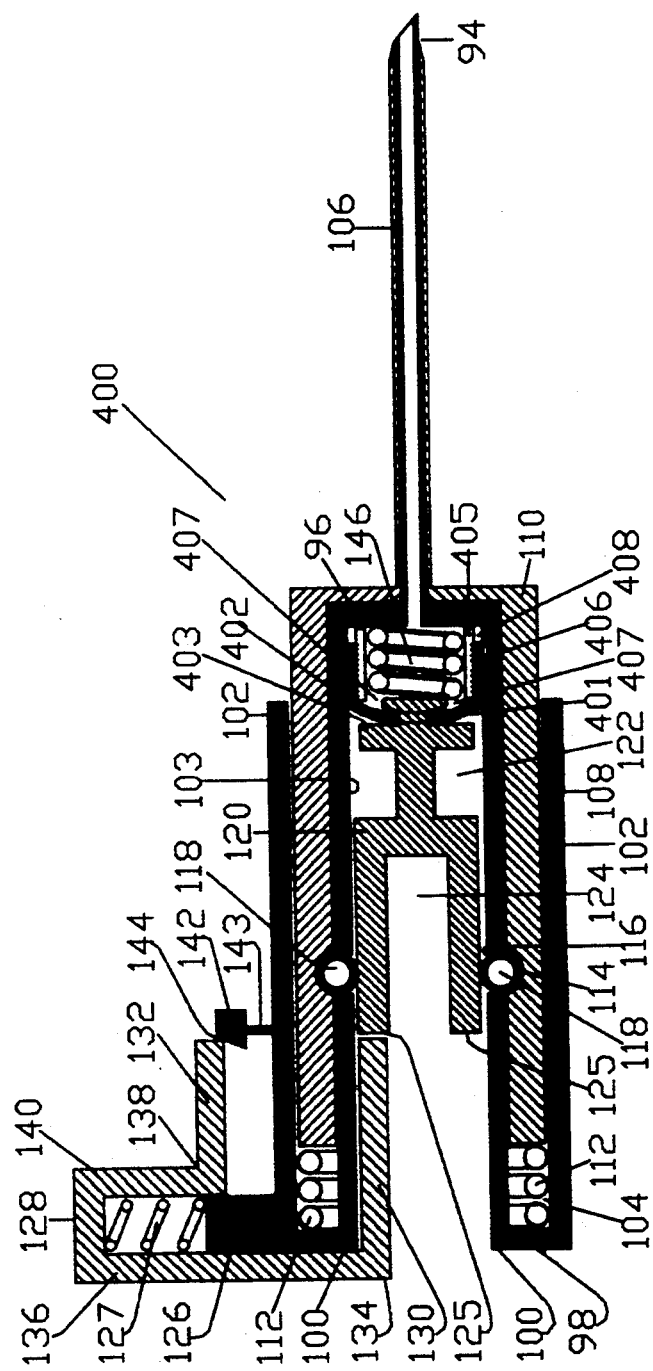
FIG. 37 is a view, similar to that of FIG. 9, showing an additional form of the catheter placement device of FIG. 9.
Figure 40:
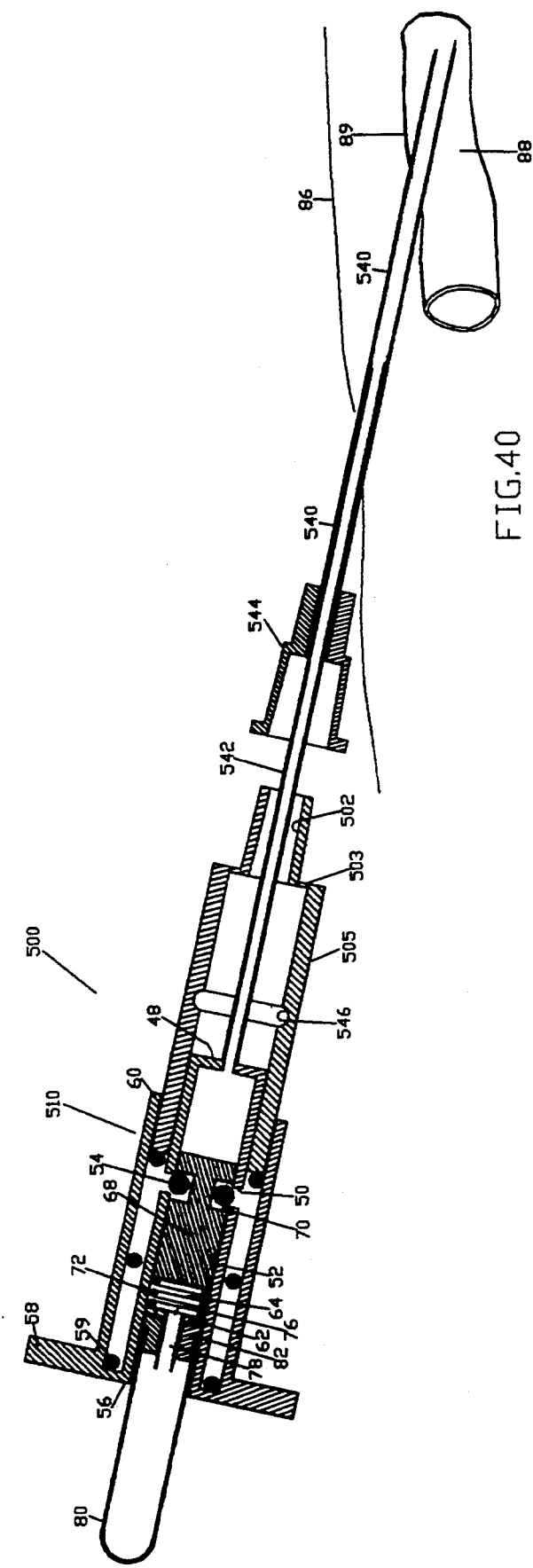
FIG. 40 is a view, similar to that of FIG. 38, showing the catheter placement device of FIG. 38 immediately after blood vessel penetration.
Figure 41:
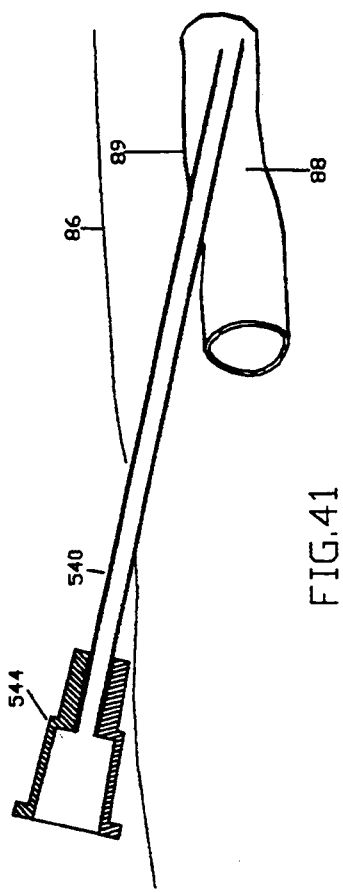
FIG. 41 is a view, similar to that of FIG. 38, showing the catheter of the catheter placement device of FIG. 38 placed intravenously.

FIG. 37 shows yet another alternative form, indicated generally at 400, of the catheter placement device of FIG. 9. The catheter placement device 400 is essentially identical to the catheter placement device 92 of FIG. 9 except that a membrane 402 of deformable material is interposed between spring 146 and piston 120. The dome 401 of membrane 402 is securely attached, via a screw or pin 404, to the anterior surface 403 of piston 120. The lateral segments 406 of membrane 402 are airtightly fitting the space 408 between the sidewall 103 of needle hub 96 and hollow cylindrical structure 405, in order to create an airtight compartment 407. Catheter placement device 400 basically functions as catheter placement device 92. When the catheter has penetrated the skin and the device is armed, spring 146 is released, causing deformation of dome 401 of membrane 402 and increasing the volume of the air-tight compartment 407, to create a vacuum within needle hub 92.

Upon blood vessel penetration, the piston 120, with attached membrane 402, no longer retained by the vacuum in space 407, will be carried rearwardly by the action of spring 146 until ball 118 enters annular recess 122. The catheter shaft 106, as described for catheter placement device 192 in FIGS. 11 and 12, is free to be displaced forward within the blood lumen by spring 112.

FIGS. 38–41 show yet another alternative form, indicated generally at 500, of the catheter placement device 39 of FIG. 5. In this version, the propelling unit or housing 510 is basically identical to needle hub 48 of catheter placement device 39 of FIG. 5. The difference between the two devices lies on the fact that the catheter hub 40 of device 39 of FIG. 9 has been replaced by a separate unit, the interface member 505, while catheter 540 has an ordinary hub 544. Said interface member 505, of a generally cylindrical shape, has an adaptor 502 protruding from the front end 503 which fits into the ordinary catheter hub 544 to which is connected. The needle 542, on the contrary, in this version, is still an integral, non detachable part of the propelling unit 510.

The sequence of operations for unit 500 is similar to that described for catheter placement device 39 of FIG. 5. In summary, after needle 542 of unit 500 has penetrated the skin 86, a vacuum is created in front of piston 68 by the arming of the device carried out by forward pressing of vacuum capsule 80 against post needle member 78 with resulting piercing of plug 82 and rearward aspiration of piston 68 with partial retraction of said piston. Upon blood vessel penetration, blood from blood vessel 88 is drawn into vacuum space or vacuum chamber 90 in front of piston 68 causing vanishing of such vacuum and full rearward retraction of piston 68 to permit ball members 54 to enter recess 70 of piston 68. Interface member 505, not any longer retained by balls 54 engaged in annular recess 546 and opening 50, will be urged to advance by spring 59, driving catheter 540, via adaptor 502 connected to catheter hub 544, further into the blood vessel. After catheter 540 is securely placed in blood vessel 88, propelling unit 510 with its interface member 505 is extracted and the catheter left in place as in FIG. 41.

Figure 42:
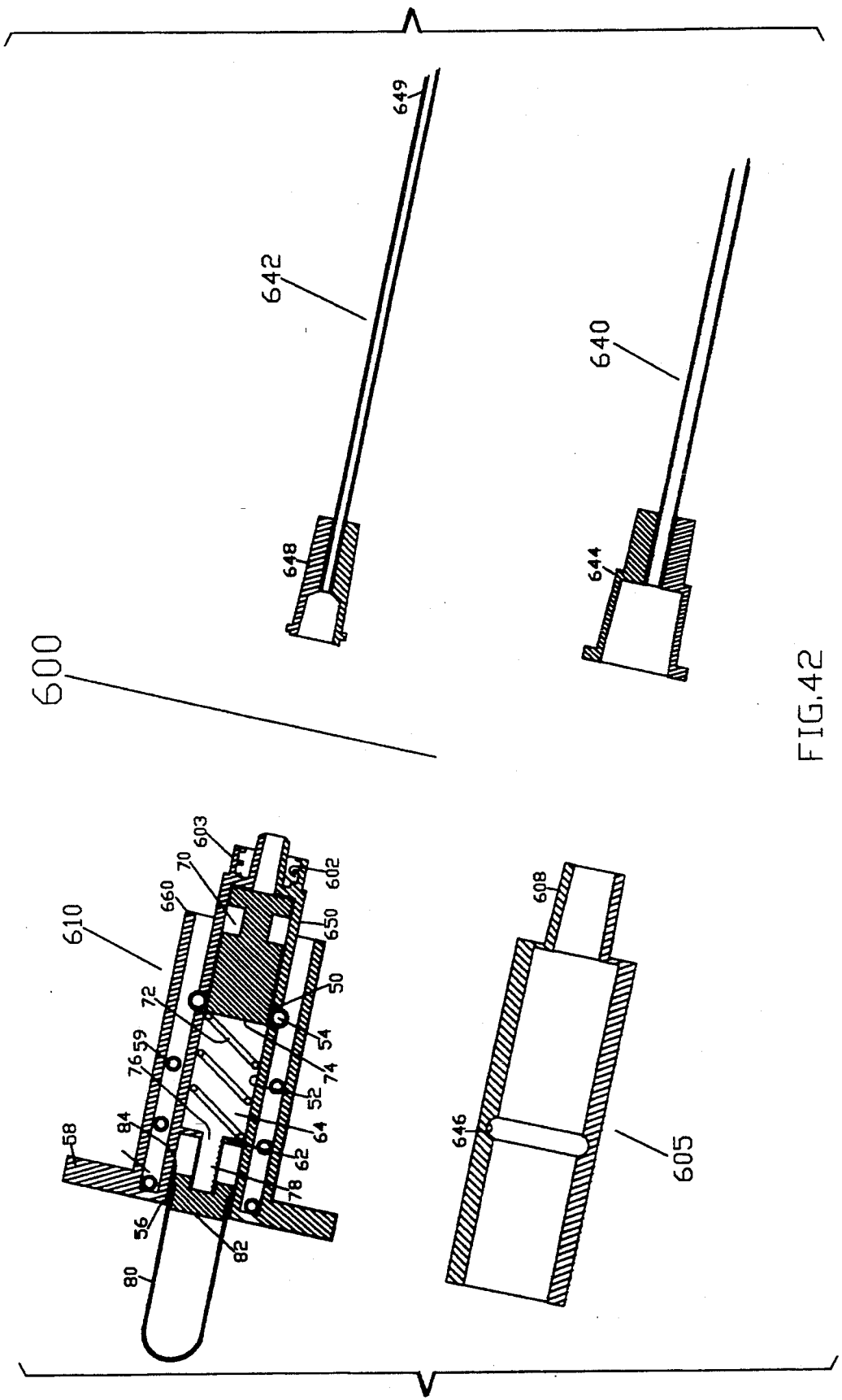
FIG. 42 shows the separate four components of a further alternative form of the catheter placement device.
Figure 43:
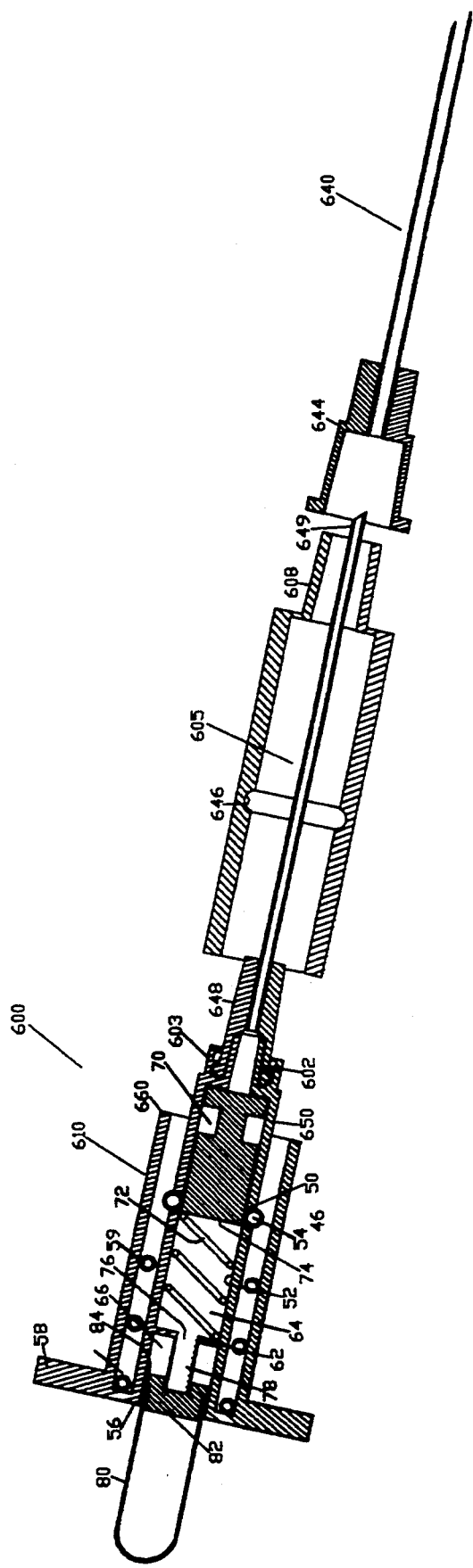
FIG. 43 shows the device of FIG. 42 while being assembled.
Figure 44:
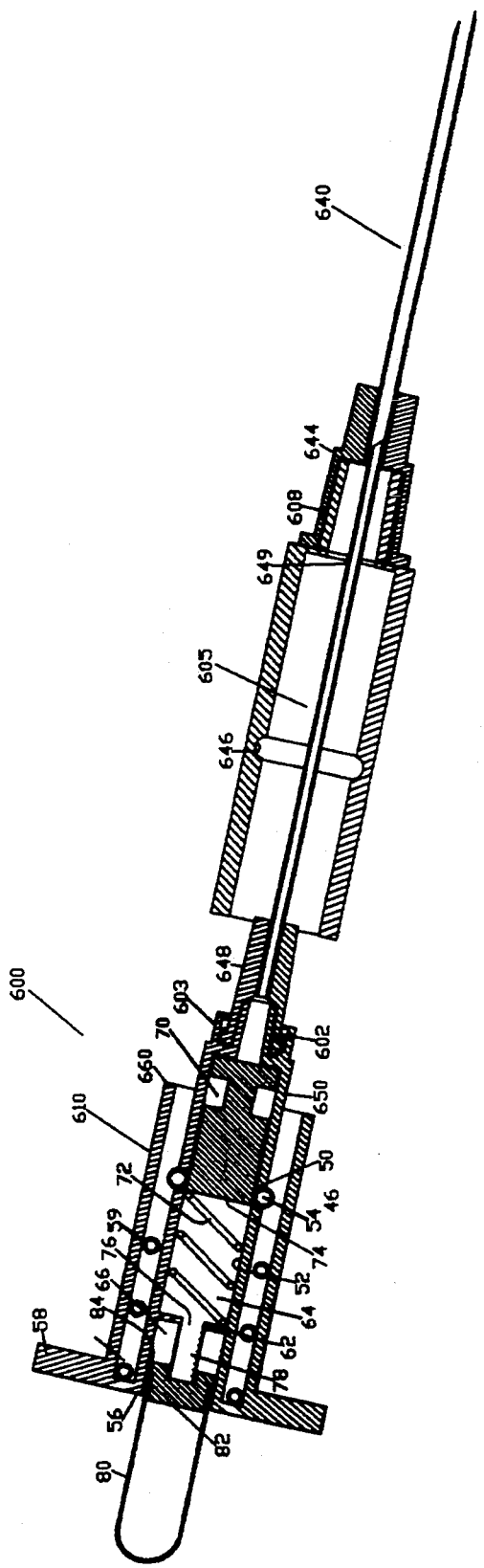
FIG. 44 shows a further stage on the assembly of catheter placement device of FIG. 42.
Figure 45:
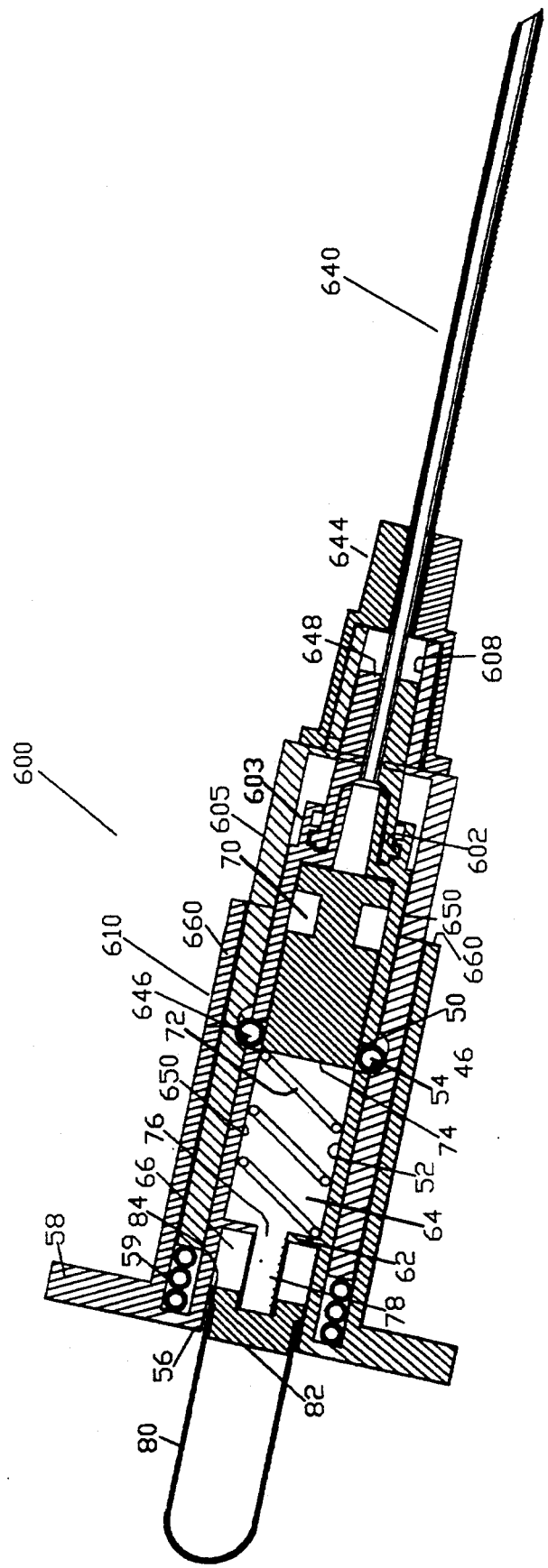
FIG. 45 shows the assembled unit of FIG. 42 prior to skin penetration.

FIGS. 42–47 show another alternative form of catheter placement device, indicated generally at 600, of the catheter placement device 39 of FIG. 5. In this version, needle 642 and catheter 640 with their respective ordinary hubs 648 and 644, are separate units from the propelling unit or housing 610. Propeller unit 610 is basically identical to needle hub 48 of device 39 of FIG. 5. An interface member 605 has replaced catheter hub 44 of device 39 of FIG. 5. FIG. 42 shows separately the four components of the device 600 prior to assembly and use: propelling unit or housing 610, ordinary needle 642, ordinary catheter 640, interface member 605. FIGS. 43, 44 and 45 show progressive stages of the assembly process. FIG. 43 shows needle 643 with ordinary hub 648 connected to adaptor 603 of propelling unit 610 via a screw type of mechanism 602, while member interface 605 and catheter 640 are shown in line ready to be connected. FIG. 44 shows catheter 640 and interface member 605 connected to each other via the fitting of the adaptor 608 of interface member 605 into ordinary catheter hub 644 of catheter 640. FIG. 45 shows the entire unit assembled and ready to be used.

Figure 46:
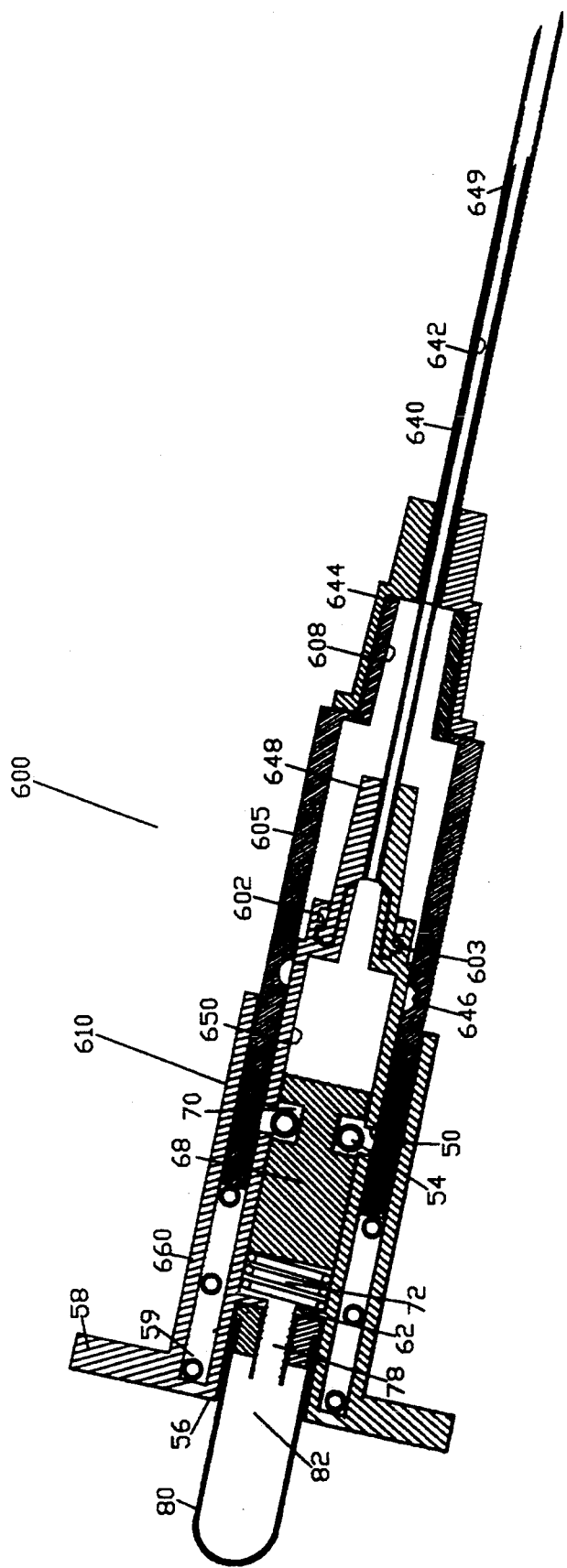
FIG. 46 shows the assembled unit of FIG. 42 after penetration into a blood vessel.
Figure 47:
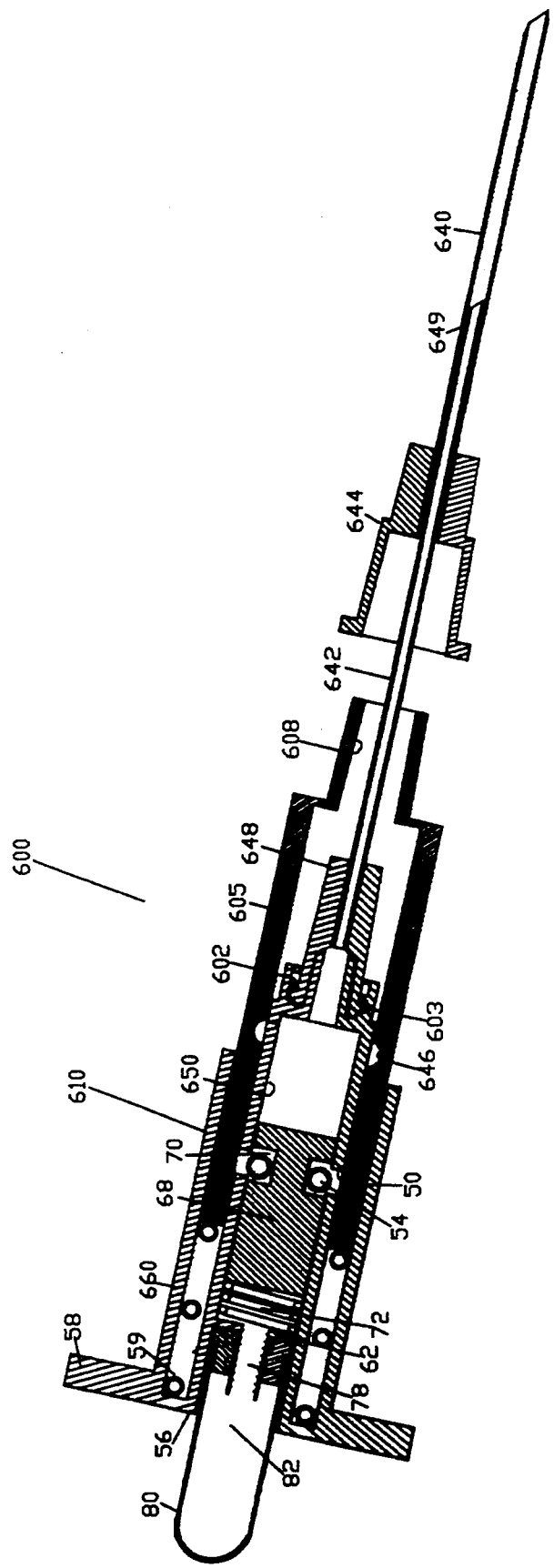
FIG. 47 shows the disengaging of the propelling unit of FIG. 42 from the catheter placed intravenously.

The sequence of operation for the placement of catheter 640 into the blood vessel is the same as the one described for the device 39 of FIG. 5 and device 500 of FIGS. 38–41. FIG. 46 shows the advancement of interface member 605 and catheter 640 upon blood vessel penetration. FIG. 47 shows the propelling unit 610 with interface member 605 extracted from the catheter 640 placed within the blood vessel.

Figure 50:
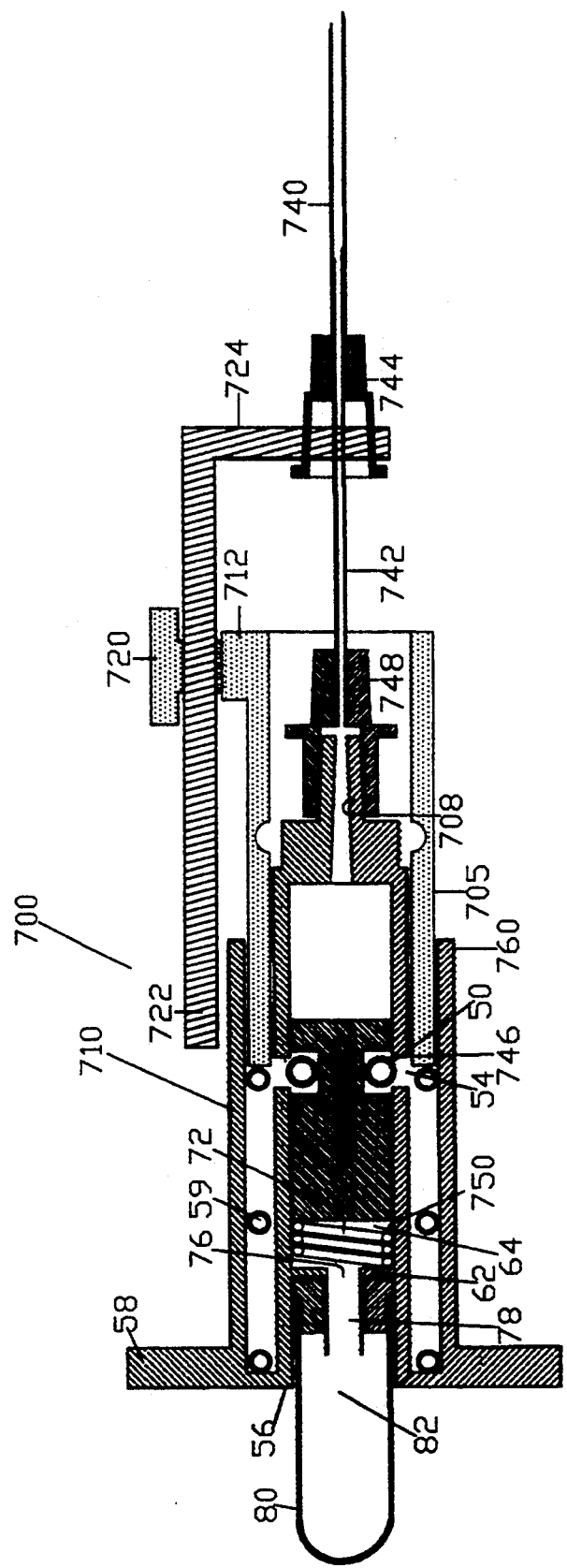
FIG. 50 shows the catheter placement device of FIG. 48 after blood vessel penetration.

FIGS. 48, 49, 50 show yet an alternative form of catheter placement device 39 of FIG. 5. In this version, generally indicated at 700, the propelling unit 710 or housing 710 is a separate unit from the catheter 740 and the needle 742 with their respective ordinary hubs 744 and 748. The separate propelling unit 710 can be applied to the catheter/needle assembly at the moment of use as needed by the operator. Propeller unit 710 is basically identical to needle hub 48 of FIG. 5, and catheter hub 44 has been replaced by interface member 705. Interface member 705 of general cylindrical hollow shape is interposed between outer wall 760 and inner wall 750 of propelling unit 710. Interface member 705 has flange 712 to which two crossed studs 722 are pivoted by pin 720 on flange 712. Arms 724 of studs 722 are applied to catheter hub 744 maintaining a secure grip on catheter hub 744 via the pressure exerted by released band spring 714 on proximal crossed segments of stud 722. FIG. 49 is a top view of device 700. The crossed studs are visualized maintaining firm grip on catheter hub 744 via arms 724.

The sequence of operation is identical to the one described for devices 39 of FIG. 5 and device 500 of FIGS. 38–41. In FIG. 50 interface member 710 urged forward by the release of spring 59 upon blood vessel penetration, will carry forward crossed studs 722 which will advance catheter 740 into the blood vessel due to the grip of arms 724 on catheter hub 744. The propelling unit 710 can be then removed from the catheter 740 releasing the grip of arms 724 on catheter hub 744 via approximating proximal segment of studs 722 against released band spring 714.

FIG. 51 and FIG. 52 show an alternative form of the semiautomatic version of the catheter placement device generally indicated at 800. In this version catheter placement device 800 includes a generally cylindrically shaped propelling unit 810 with an inner hollow cylinder 814 with a front end 816 supporting needle 840 and an outer cylinder 812, concentric to inner cylinder 814, bearing flange 822 and lever 844 and enclosing, for the purpose of visualizing backflow of blood, a transparent chamber 826 containing vacuum capsule 830. Catheter placement device 800 includes also catheter 860 with ordinary catheter hub 862 and an interface member 850 interposed between outer cylinder 812 and inner cylinder 824, provided with adaptor 852 fitting into ordinary catheter hub 862. FIG. 51 shows device 800 in its armed position after skin penetration. Arming is obtained by pressing forward vacuum capsule 830 against posterior segment 842 of needle 840 causing the piercing of plug 832 of capsule 830 by said posterior segment 842. FIG. 52 shows device 800 after blood vessel penetration. Upon blood vessel penetration, vacuum 834 within capsule 830 will draw blood into transparent vacuum capsule 830. Presence of blood in capsule 830 will alert the operator of the occurred blood vessel penetration and he or she will promptly press handle 844 of lever 824 pivoted on fulcrum 846, causing disengagement of tooth 844 out of recess 856 of interface member 850. Disengagement of tooth 844 will permit advancement of interface member 840 by action of spring 818 and placement of its connected catheter 860 within blood vessel 89.

FIGS. 53 through 59 show alternative types of catheter placement devices in which means of sensing penetration comprises various types of transducers activated by backflow of the blood occurring upon penetration of the blood vessel. In the following figures, transducers have been represented in conjunction with a vacuum chamber accelerating the backflow. However, naturally, transducers can work as well without the presence of the vacuum chamber.

Figure 53:
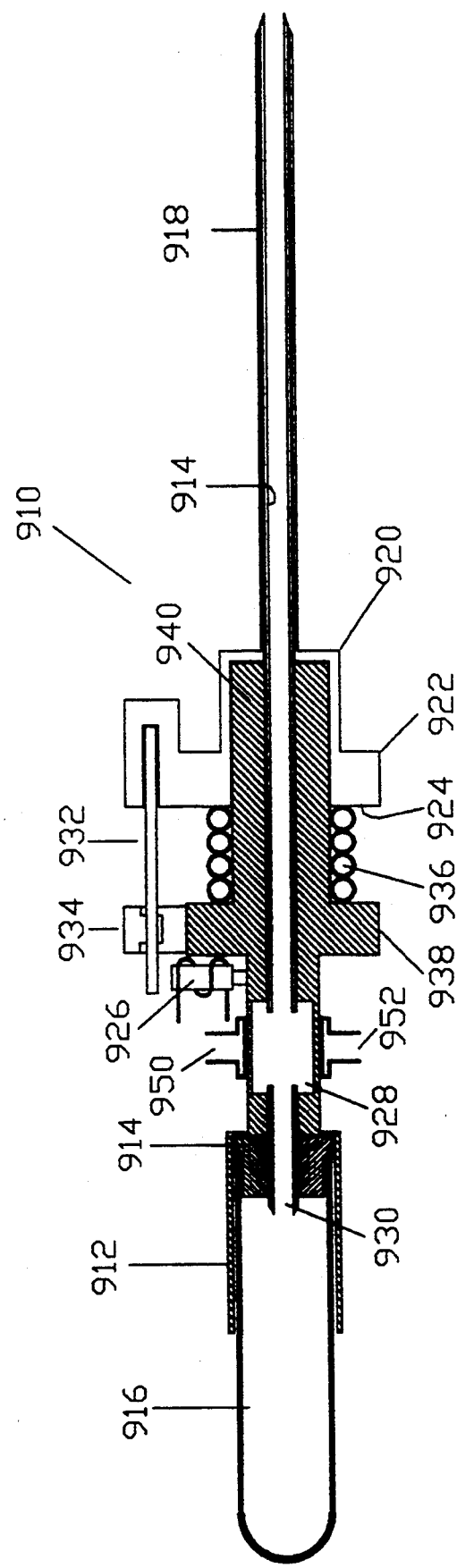
FIG. 53 shows yet an alternative form of a fully automatic catheter placement device, where the means for sensing penetration are represented by an opto-electric source-sensor pair.

FIG. 53 shows a schematic version of the device in which an optical-photosensor senses the occurred penetration of the blood vessel by optically detecting the blood rushing into the detection chamber. The optical-photosensor pair, source/sensor chosen for representation in FIG. 53 includes a light emitting device, 950, and a light sensor, 952. Transduction of light stimuli captured by light sensors 952 in response to passage of the blood within detection chamber 928 may be variously obtained by various transduction elements, like photovoltaic, photoconductive, photoconductive junction, photoemissive. Transducers will in turn activate electromagnet 925 to displace metal lever 932 of FIG. 53 by attraction toward its pole effacing the lever, disengaging in so doing lever 932 from its retainer 934, and permitting forward advancement of the catheter 918 by the resiliency of compressed spring 936 acting upon flange 938 of needle hub 940 and flange 922 of catheter hub 920. The light sensor 952 of FIG. 53 may be placed on the same side as light emitting device 950. In that case the light sensor 952 will detect a beam reflected from the opposite wall of the detection chamber, which in that case acts as reflecting surface, or by the blood itself that will reflect the light beam by diffusion. The light sensor 952 placed on the same side as the light emitting device.

Figure 54:
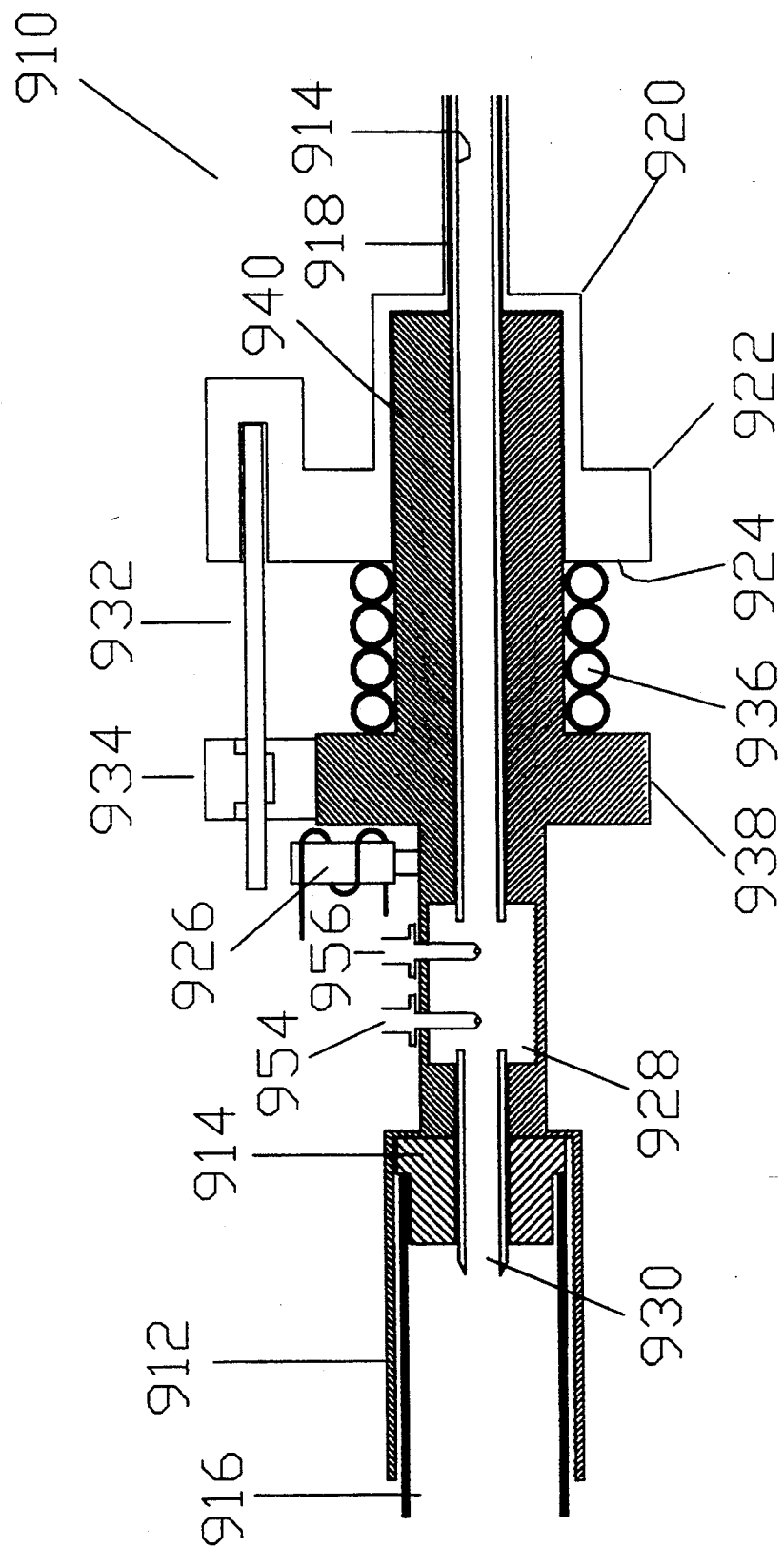
FIG. 54 show an alternative form of the device of FIG. 53 where the represented sensors are temperature sensors.

FIG. 54 shows a device substantially similar to device of FIG. 53, where temperature sensors, rather than optical sensors, sense the occurred penetration of the blood vessel by detecting the variation of temperature induced on temperature sensors 954 and 956 of FIG. 54 by the warm blood rushing into the detection chamber. The temperature sensors chosen for representation in FIG. 54 are sensors responding to heat transfer method of conduction from blood to sensors, however temperature sensors acting upon heat transfer method of convection as well as sensors acting upon heat transfer method of radiation can also be used. Transduction elements may be thermoelectric elements, resistive elements, oscillating crystals elements, and others.

Figure 55:
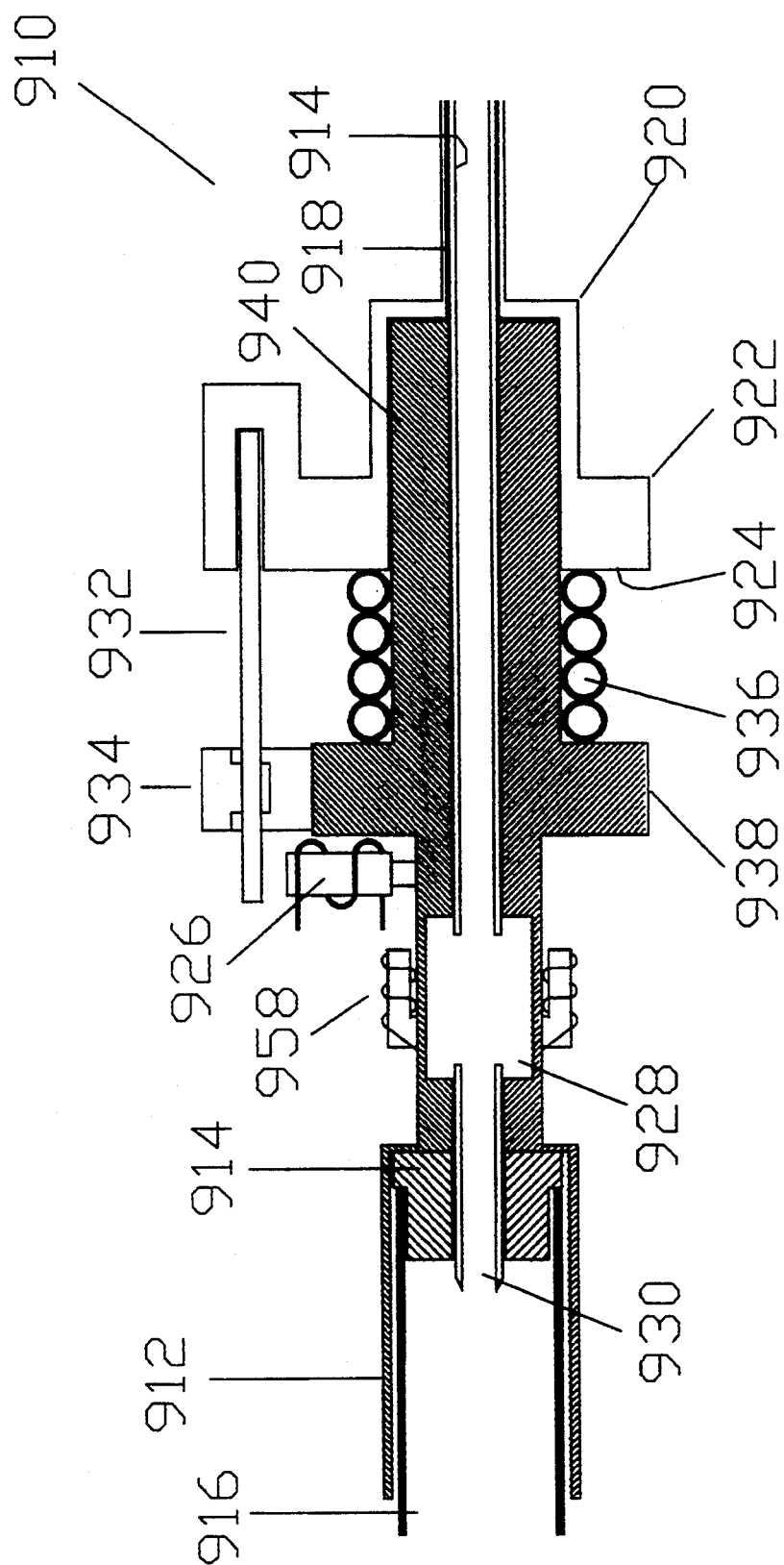
FIG. 55 show an alternative form of the device of FIG. 53 where the represented sensors are sensors detecting the electrical conductivity properties of the blood.

FIG. 55 shows a device substantially similar to device of FIG. 53, where sensors detecting blood as an electric conductor, rather than optical sensors, sense the occurred penetration of the needle into a blood vessel by detecting the appearance of an electrical conductor, such as blood, rushing into the detection chamber. The sensors chosen in FIG. 55 to illustrate the detection of the physical property of conductivity of the blood include an electromagnet, 958. Detection chamber 928 is between the poles of electromagnet 958. The blood rushing into the detection chamber upon needle penetration of a blood vessel is detected by an application of the principle that a voltage proportionate to the rate of flow is induced in a conductor moving through a magnetic field at right angles to the magnetic lines of forces. Transduction is achieved by inductance, capacitance, resistance. Blood could also behave as a dielectric and as such the rushing of the blood into the detection chamber could be detected by capacitance transducers where the passage of blood results in changes of voltages at the electrodes of the capacitor.

Figure 56:
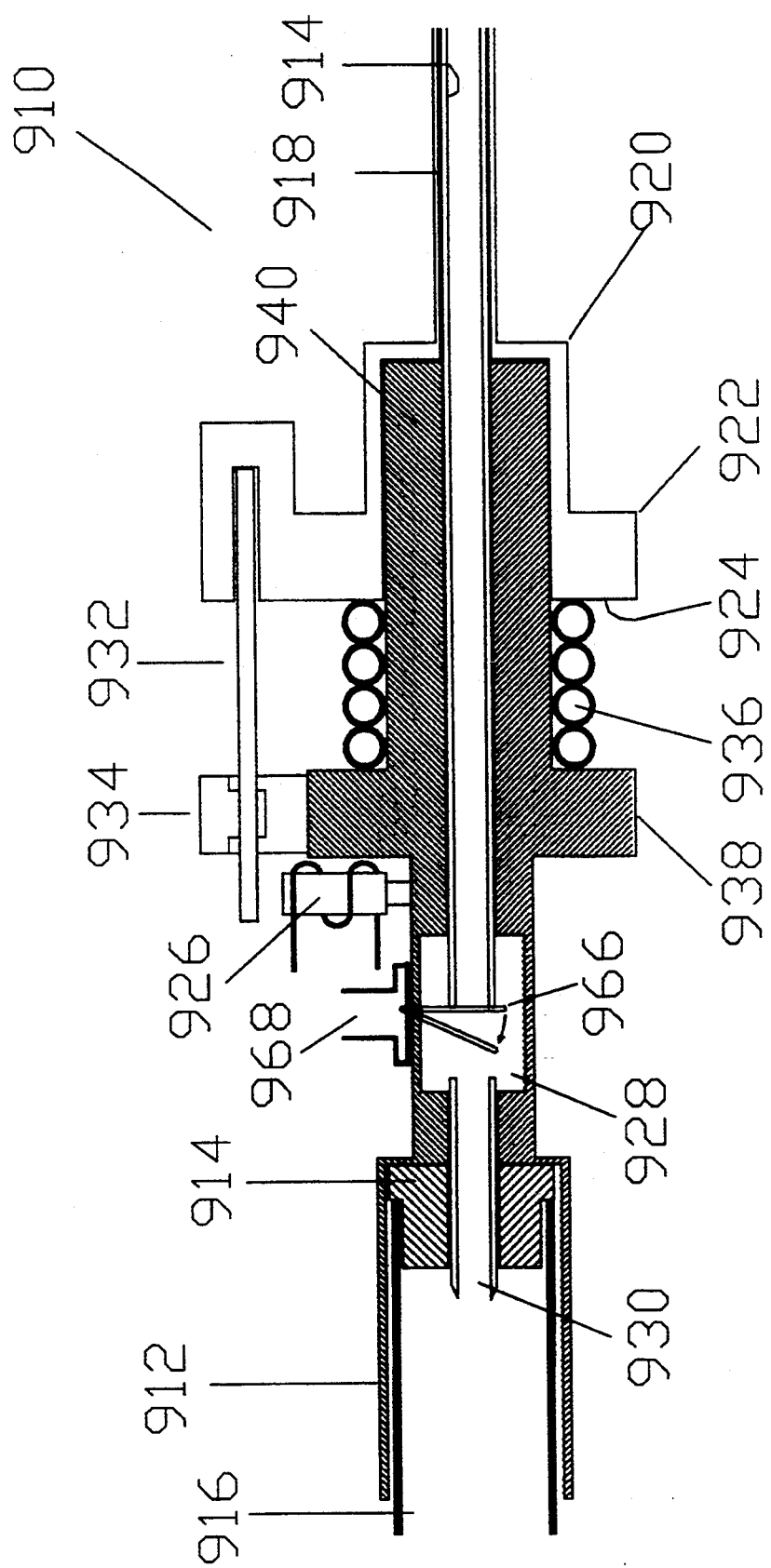
FIG. 56 shows an alternative form of the device of FIG. 53 in which the represented sensor is a flow detector sensor.

FIG. 56 shows a device substantially similar to device of FIG. 53, where sensors detect the physical property of the blood as a fluid. The sensor chosen in FIG. 56 to illustrate detection of blood as a flowing fluid is mechanical flow sensing element 966, whose angular displacement is caused by the rushing of the blood into detection chamber 928 upon blood vessel penetration. Such a displacements may activate a switch which in turn will activate electromagnet 926. Other type of sensor detecting the physical property of the blood as a fluid can be used, such as other types of flow sensors, fluid density sensors, humidity and moistures sensors, hygrometers, and others. Transduction elements are of most various types and depend upon the type of sensing element used.

Figure 57:
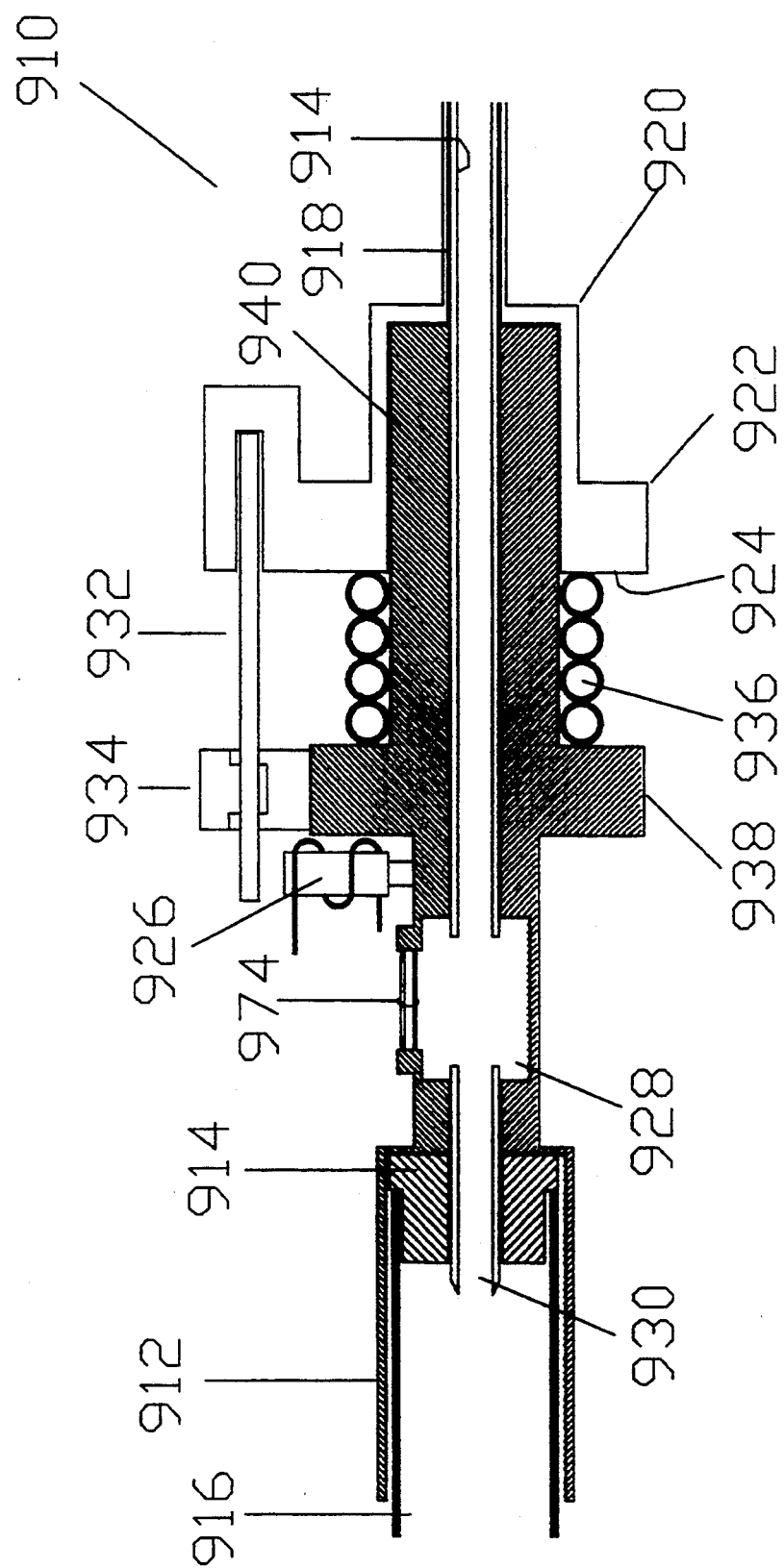
FIG. 57 shows an alternative device of FIG. 53, where the represented sensor is an acoustic sensor.

FIG. 57 shows a device substantially similar to device of FIG. 53, where sensors detecting static and dynamic acoustic properties of the blood. The sensors chosen in FIG. 57 illustrate the presence of the blood via detecting the sound generated by the blood rushing into detection chamber 928 by acoustic sensor 974. Sensors based on ultrasound/sonar technics can also be used to detect blood rushing into detection chamber upon blood vessel penetration.

Figure 58:
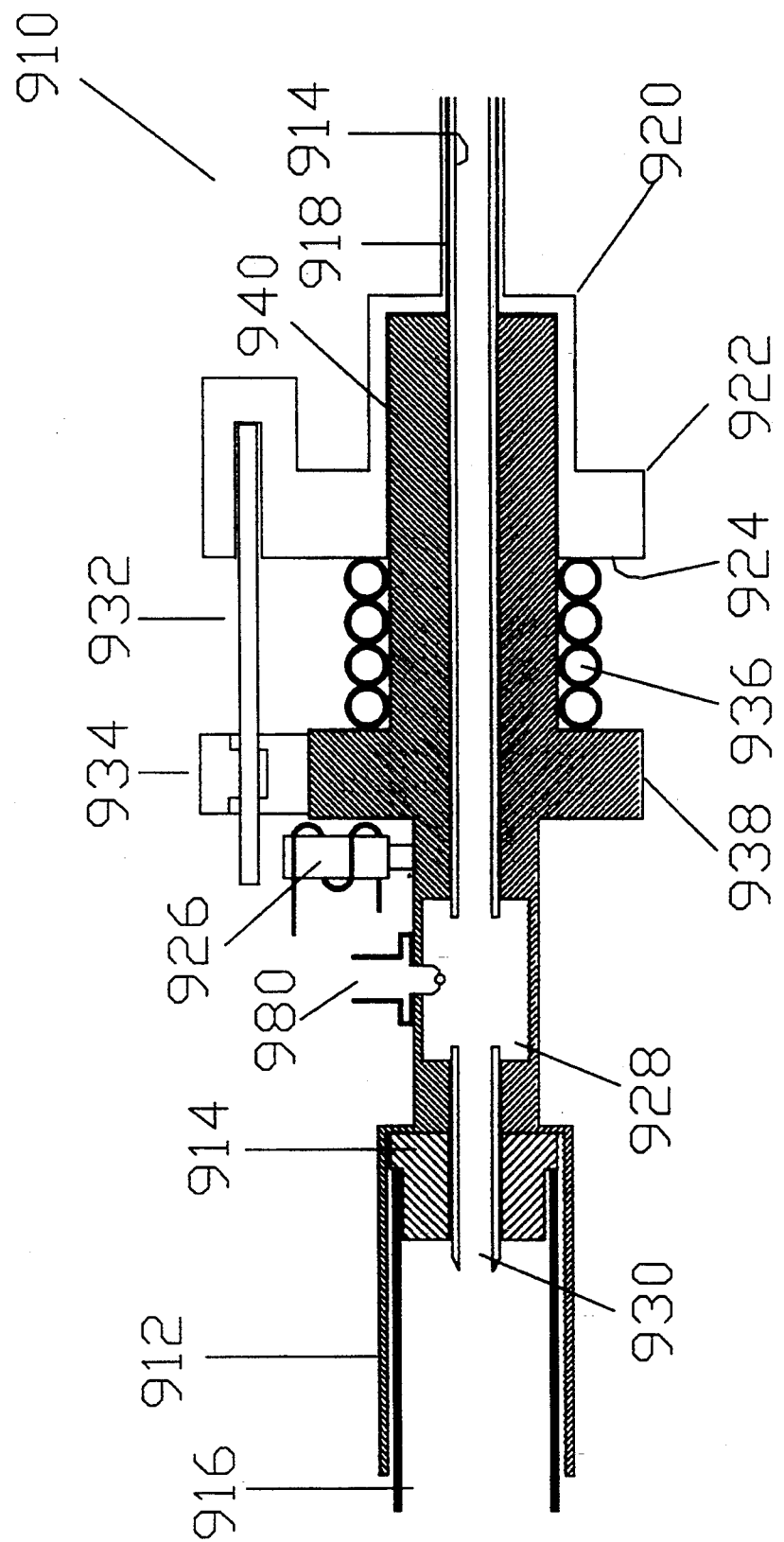
FIG. 58 shows yet an alternative form of the device of FIG. 53 in which the represented sensor is a pressure sensor.

FIG. 58 shows pressure/vacuum transducers, 980, activated by the change in pressure in detection chamber 928 occurring upon blood vessel penetration. The pressure transducers may be of various types: capacitative, inductive, piezoelectric, potentiomentric, reluctive, straingage, servo-type, of vibrating elements, and others.

Figure 59:
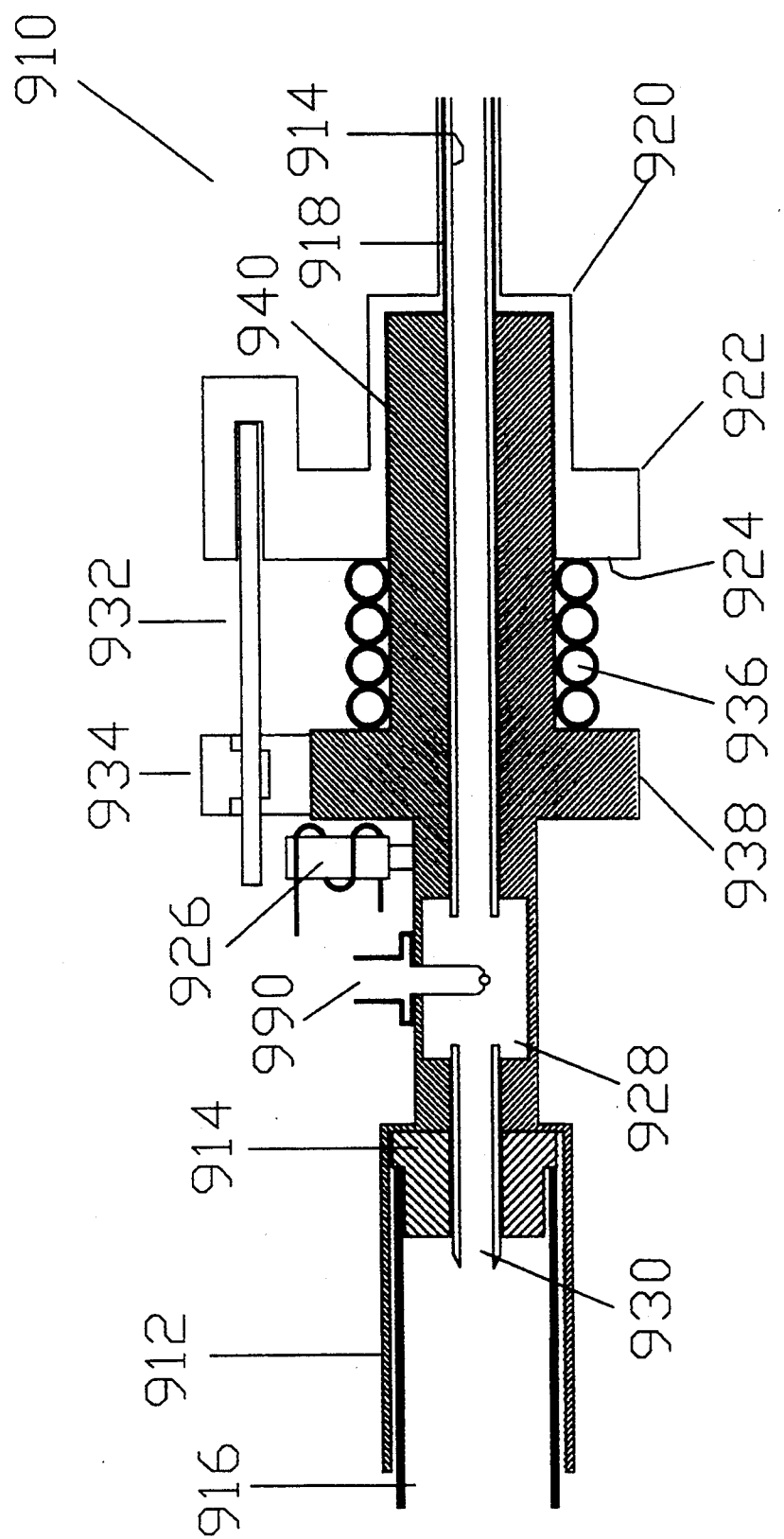
FIG. 59 shows yet an alternative form of the device of FIG. 53 in which the represented sensor is an illustration of a sensor of chemical properties of the blood, such as a pH sensor, or of a sensor capable of sensing presence of blood by detecting presence of a component of the blood, such as oxygen.

FIG. 59 shows yet an alternative form of the device of FIG. 53 in which the represented sensor 990 is an illustration of a sensor of chemical properties of the blood, such as a sensor able to detect certain ranges of pH, characteristic of the blood. Other kinds of chemical properties of the blood are susceptible to be detected with the appropriate sensors, as well as physiological properties of the blood. Blood could also be detected by detecting blood components with the use of appropriate sensors analizers, such as the 02 sensor 990 of FIG. 59. Sensors analizers could identify blood presence by any of the technics used to analize blood components. The blood components that can be used for blood detection are all the blood components which can be quickly identified by analizers.

Obviously, numerous other variations and modifications can be made without departing from the spirit of the present invention. Therefore, it should be clearly understood that the forms of the present invention described above and shown in the figures of the accompanying drawing are illustrative only and are not intended to limit the scope of the present invention.

What is claimed is:

1. An intravascular catheter placement device for insertion of an intravascular catheter into the interior of a blood vessel comprising:
   an intravascular catheter;
   a hollow needle, said catheter being concentric to said hollow needle;
   means self initialed and for self-propelled advancement of said intravascular catheter into the interior of a blood vessel.

2. The intravascular catheter placement device of claim 1 further comprising:
   a chamber, wherein the pressure within said chamber is a vacuum pressure, said chamber being in communication with said hollow needle.

3. The device of claim 2 further comprising:
   means for actuating said self-propelled means for self-propelled advancement of said catheter into the interior of a blood vessel, upon backflow of blood occuring upon blood vessel penetration, said blood being drawn by said vacuum pressure within said chamber.

4. The device of claim 3 wherein: said actuating means are automatically actuable means to actuate said self-propelled means for self-propelled advancement of said catheter into the interior of a blood vessel, in response to backflow of blood occurring upon blood vessel penetration, said blood being drawn by said vacuum pressure within said chamber.

5. The device of claim 4 further comprising:
   sensing means, sensing the backflow of blood toward said chamber upon blood vessel penetration by said hollow needle to cause said actuating means to automatically actuate said self-propelled means to advance said intravascular catheter into the interior of the penetrated blood vessel.

6. The device of claim 5 wherein: said sensing means are means sensing pressure changes, said pressure changes resulting from the backflow of blood into said chamber upon blood vessel penetration by said hollow needle, said means sensing pressure changes causing the actuating means to automatically actuate said self-propelled means to advance said intravascular catheter into the interior of the penetrated blood vessel.

7. The device of claim 5 wherein: said sensing means are transducers means sensing backflow of blood occurring upon blood vessel penetration by said hollow needle, said transducers causing the actuating means to automatically actuate said self-propelled means to advance said intravascular catheter into the interior of the penetrated blood vessel.

8. The device of claim 2 wherein said self-propelled means is resilient.

9. The device of claim 2 wherein said self-propelled means is magnetic.

10. The device of claim 2 wherein said self-propelled means is pneumatic.

11. The device of claim 10 wherein said pneumatic means employs compressed air.

12. The device of claim 2 wherein said self-propelled means is expandable material.

13. The device of claim 12 wherein said expandable material is thermally expandable.

14. The device of claim 2 wherein said self-propelled means is hydraulic.

15. The device of claim 2 wherein said self-propelled means is a cam means.

16. The device of claim 2 wherein said self-propelled means is a lever means.

17. The device of claim 2 wherein said needle comprises a hollow shaft projecting forward from a needle hub, said needle hub being adapted to house said chamber communicating with said hollow needle; and wherein said intravascular catheter comprises a hollow catheter shaft slideable along said hollow needle, and a catheter hub, slideable along said needle hub and said needle shaft, said hollow catheter shaft projecting from said catheter hub.

18. The device of claim 2 further comprising:
   a housing wherein said chamber and said propelling means are housed, said hollow needle projecting forward from said housing and communicating with said chamber; said intravascular catheter comprising a hollow catheter shaft slideable along said hollow needle, and a catheter hub adapted to engage with said propelling means, said hollow catheter shaft projecting from said catheter hub.

19. The device of claim 2 further comprising:
   is a housing wherein said chamber and said propelling means are housed, said chamber having at least one opening leading to an adaptor projecting from said housing, said hollow needle comprising a hollow shaft projecting from a needle hub, said needle hub being adapted to couple in airtight fashion with said adaptor projecting from the housing; said intravascular catheter comprising a hollow catheter shaft slideable along said hollow needle, and a catheter hub adapted to engage with said propelling means, said hollow catheter shaft projecting from said catheter hub.

20. The device of claim 2 wherein said intravascular catheter comprises:
   a hollow catheter shaft slideable along said hollow needle, and
   a catheter hub, said catheter shaft projecting from said catheter hub.

21. The device of claim 2 further comprising a housing wherein said chamber and said self-propelling means are housed; an interface member between said propelling means and said catheter; said hollow needle communicating with said chamber projecting forward from said housing; said catheter including a hollow catheter shaft slideable along the needle, and a catheter hub, said catheter shaft projecting from said catheter hub.

22. The device of claim 21, wherein said interface member is joined to said catheter into a single unit.

23. The device of claim 21 above, wherein said interface member is joined to said propelling means into a single unit.

24. The device of claim 2 further including:
a housing wherein said chamber and said propelling means are housed, said chamber having at least one opening leading to an adaptor projecting from said housing,
said hollow needle comprising a hollow shaft projecting from aneedle hub, said needle hub being adapted to couple in airtight fashion with said adaptor projecting from said housing;
an interface member between said propelling means and said catheter, said catheter comprising a hollow catheter shaft slideable along the needle, and a catheter hub, said hollow catheter shaft projecting from said catheter hub.

25. The device of claim 24, wherein said interface member is joined to said catheter into a single unit.

26. The device of claim 24, wherein said interface member is joined to said propelling means into a single unit.

27. The device of claim 2 wherein said chamber is a vacuum chamber.

28. The device of claim 1, further comprising:
means for creation of a pressure below the atmospheric pressure within a chamber in communication with said hollow needle.

29. The device of claim 2 further comprising:
means for creation of said vacuum pressure.

30. The device of claim 29 wherein said means for creation of a vacuum pressure comprises:
a piston axially slideable within said chamber communicating with said hollow needle, wherein rearward displacement of said piston creates a vacuum pressure in said chamber.

31. The devioe of claim 29 wherein said means for creation of a vacuum pressure comprises:
a piston axially slideable within said chamber communicating with said hollow needle, said piston being urged rearwardly to a partially retracted position to create a vacuum pressure forward of said piston, by resilient means actuable subsequently to skin penetration of said hollow needle and prior to penetration of a blood vessel.

32. The device of claim 29 wherein said means for creation of a vacuum pressure comprises:
a piston axially slideable within said chamber communicating with said hollow needle, said piston being manually displaceable to create a vacuum pressure in front of said piston to cause backflow of blood upon blood vessel penetration, thereto to manually actuate the self-propelling means.

33. The device of claim 29 wherein said means for the creation of a vacuum pressure comprises:
a piston slideable within said chamber,
a post-needle member projecting from a wall delimiting said chamber,
a vacuum capsule mounted adjacent said wall and pierceable by said post-needle member after skin penetration by said hollow needle and prior to penetration of a blood vessel to allow air from said chamber to pass into said capsule to create a vacuum pressure in said chamber to draw said piston partially rearward and so to create a vacuum pressure within said chamber forward of said piston to cause blood to flow into said hollow needle immediately upon blood vessel penetration by said hollow needle.

34. The device of claim 29, wherein said means for creation of a vacuum pressure comprises:
a piston slideable axially within said chamber,
a hollow needle carried by said piston extending for the whole length of said piston and rearwardly projecting from said piston, said hollow needle being in communication of said chamber in front of the piston,
a vacuum capsule having a plug pierceable by said rearwardly projecting hollow needle, said plug initially closing airtightly posteriorly said projecting hollow needle, said capsule being slideable toward the piston to have said plug pierced by said projecting hollow needle, to cause air to pass into said capsule from said chamber in front of said piston, to create a vacuum pressure within said chamber in front of said piston.

35. The device of claim 29 wherein said means for creation of a vacuum pressure comprises:
at least one deformable wall defining said chamber communicating with said needle, said wall being deformable to increase the volume of said chamber thereto to create a vacuum pressure within said chamber.

36. The device of claim 29 wherein said means for the creation of a vacuum pressure comprises:
a vacuum capsule having a plug pierceable by a posterior segment of said hollow needle, after skin penetration creating a vacuum pressure within said hollow needle.

37. The device of claim 29 wherein said means for creation o.fvacuum pressure comprises:
a hollow piston slideable over said chamber communicating with said hollow needle, resilient means urging said hollow piston rearwardly to increase the volume of said chamber to create a vacuum pressure within said chamber.

38. The device of claim 29 further comprising:
means for arming said means for the creation of said vacuum pressure.

39. The device of claim 38 wherein said arming means is manually actuable.

40. The device of claim 39,
wherein said needle comprises a hollow shaft projecting forward from a needle hub, said needle hub being adapted to house said chamber communicating with said hollow needle;
wherein said intravascular catheter comprises a hollow catheter shaft slideable along said hollow needle, and a catheter hub slideable along said needle hub and said needle shaft, said hollow catheter shaft projecting from said catheter hub;
wherein said manually actuable arming means comprises:
a trigger member engaging a stud projecting radially outwardly from said needle hub, and manually movable between a first position and a second position,
a rearwardly opening recess extending axially of a piston slideable within said chamber,
resilient means urging said piston to a partially retracted position,
a first flange carried by said trigger member extending to a position engageable with said piston, when said trigger member is in said first position to lock said piston in its advanced position and moveable into said rearwardly opening recess when said trigger member is in its second position to allow said resilient means to move said piston to its fully retracted position by the vanishing of said vacuum pressure.

41. The device of claim 39 wherein said manually actuable arming means comprises:
a lever retaining a vacuum creating piston in advanced position, said piston being slideable within said chamber, said lever being released manually after skin penetration to disengage said piston to be displaced rearwardly by resilient means to create a vacuum pressure in front of said piston.

42. The device of claim 39 wherein said manually actuable arming means comprises:
a vacuum capsule having a plug pierceable by a posterior segment of said hollow needle, being manually slideable toward said posterior segment of hollow needle, to have said plug pierced by said hollow needle after skin penetration, said plug being made of material airtightly sealing around the piercing needle, to create a vacuum pressure within said hollow needle.

43. The device of claim 38 herein said arming means is automatically actuable in response to skin penetration.

44. The device of claim 43 wherein said automatically actuable arming means comprises:
a sleeve telescopically slideable over said catheter said sleeve having a distal end of sufficient thickness to be retained from advancing with the catheter during skin penetration and a proximal end notch to releasably engage a hook connected to a vacuum pressure creating hollow piston slideable over said chamber, said piston being urged rearwardly by a resilient means, said tooth being disengageable by rearward sliding of said sleeve to allow said hollow piston to be displaced rearwardly by said resilient means.

45. The device of claim 4, wherein said automatically actuable means are automatically responsive to rearward movement of a piston slideable within said chamber in response to pressure change resulting from the backflow of blood into said chamber to allow advancement of said intravascular catheter by said self-propelled means.

46. The device of claim 4,
wherein said needle comprises a hollow shaft projecting forward from a needle hub, said needle hub being adapted to house said chamber communicating with said hollow needle;
wherein said intravascular catheter comprises a hollow catheter shaft slideable along said hollow needle, and a catheter hub, slideable along said needle hub and said needle shaft, said hollow catheter shaft projecting from said catheter hub;
wherein said means automatically actuating said self-propelling means to advance said intravascular catheter comprises:
at least one ball member mounted in an opening formed in a side wall of said chamber, said ball member in said opening releasably locking the intravascular catheter by protruding from said opening into an annular recess extending about the interior of said catheter hub, said catheter hub being slideable about said chamber, said ball member being retained in said annular recess by a piston slideable within said chamber. Said ball member then unlocking the intravascular catheter, when the opening where said ball member is mounted aligns with a correspondent annular recess formed on said piston, being said ball member no longer retained in the annular recess of the catheter hub by the rearwardly displaced piston resulting from backflow of blood into said chamber.

47. The device of claim 4,
wherein said needle comprises a hollow shaft projecting forward from a needle hub, said needle hub being adapted to house said chamber communicating with said hollow needle;
wherein said intravascular catheter comprises a hollow catheter shaft slideable along said hollow needle, and a catheter hub, slideable along said needle hub and said needle shaft, said hollow catheter shaft projecting from said catheter hub;
wherein said means automatically actuating said self-propelling means to advance said intravascular catheter comprises:
a resilient hook anchored to said catheter hub, said catheter hub being urged forward by said propelling means, said needle having an external hub concentrically built around said hub, said resilient hook releasably engaged in a hole formed in said external needle hub to retain said catheter from being advanced by said propelling means, said hook being disengageable from said hole by a flange protruding outwardly from a hollow piston slideable between the hubs, upon rearward displacement of said piston, said piston being airtightly slideable on said hub, said rearward displacement of the piston resulting from the vanishing of a vacuum pressure caused by the backflow of blood into said vacuum pressure chamber occurring upon blood vessel penetration, said vacuum pressure opposing the action of resilient means urging said piston rearwardly prior to blood vessel penetration.

48. The device of claim 4 wherein:
a piston slideable within said chamber in an airtight fashion , said airtight fashion resulting from the action of a sealing ring of resilient material annularly extending about said piston, said ring being compressed on said piston by said chamber, said piston having a posterior member engaging with the self-propelling means rearwardly of said piston to actuate said self-propelling means upon an accelerated rearward displacement of said piston , said piston being urged rearwardly by resilient means, said accelerated rearward displacement resulting from the engagement of said piston into an expanded posterior portion of said chamber, said expanded portion of the chamber lessening the compression exerted upon the sealing ring by the narrower anterior portion of said chamber, said lessening of compression resulting in a suddenly decreased resistance to the rearward displacement of said piston, resulting in turn into an accelerated rearward displacement of said piston.

49. The device of claim 4 wherein said automatically actuating means comprises:
an electromagnet automatically activated by sensing means detecting backflow of blood toward said chamber to release said propelling means to advance said intravascular catheter into the interior of a blood vessel.

50. The device of claim 4 wherein said means actuating said self-propelling means to advance said intravascular catheter comprises:
at least one ball member mounted in an opening formed in a side wall of said chamber, said ball member in said opening releasably locking an interface member interposed between said propelling means and said catheter, due to the protruding of said ball member from said opening into an annular recess formed in said interface member, said interface member being slideable about said chamber, said ball member being retained in said annular recess by a piston slideable within said chamber. Said ball member causing the unlocking of the interface member upon alignment of the opening where said ball member is mounted with a correspondent annular recess formed on said piston, said ball member being no longer retainable in the annular recess of the interface member by the rearwardly displaced piston resulting from backflow of blood into said chamber.

51. The device of claim 2, further comprising:
means for identifying penetration of a blood vessel.

52. The device of claim 2 further comprising:
means for sensing penetration of a blood vessel by said hollow needle.

53. The device of claim 6 wherein said means for sensing pressure changes comprises:
means for sensing the vanishing of said vacuum pressure occurring upon blood vessel penetration, within said chamber communicating with said hollow needle, said means being responsive thereto to automatically actuate said means for self-propelled advancement of said catheter.

54. The device of claim 6 wherein said means sensing pressure changes includes:
a piston slideable within said chamber, and retained in an advanced position by the presence of said vacuum pressure in front of said piston, said piston being rearwardly displaceable upon the fall of pressure within said chamber in front of the piston caused by the backflow of the blood drawn by the vacuum pressure into said chamber occurring upon blood vessel penetration.

55. The device of claim 6 wherein said means sensing pressure changes includes
a piston slideable within said chamber, and retained in an advanced position by the presence of a vacuum pressure in front of said piston, being said piston rearwardly displaceable by said resilient means upon the fall of pressure within said chamber in front of the piston caused by the backflow of the blood drawn by the vacuum pressure into said chamber occurring upon blood vessel penetration.

56. The device of claim 6 wherein said means sensing pressure changes includes:
a piston slideable within said chamber, and retained in an advanced position by the presence of a vacuum pressure in front of said piston, said piston being manually displaceable upon the fall of pressure within said chamber in front of the piston caused by the backflow of the blood drawn by the vacuum pressure into said chamber occurring upon blood vessel penetration.

57. The device of claim 7 wherein said transducers means sensing the backflow of blood, activates an electromagnet to release said self-propelled means to advance said intravascular catheter into the interior of a blood vessel.

58. The device of claim 7 wherein said transducers means sensing the backflow of blood, occurring upon blood vessel penetration, comprises:
optical sensing means.

59. The device of claim 7 wherein said transducers means sensing the backflow of blood, occurring upon blood vessel penetration, comprises:
temperature sensing means.

60. The device of claim 7 wherein said transducers means sensing the backflow of blood, occurring upon blood vessel penetration, comprises:
means for sensing electrical properties of the blood.

61. The device of claim 7 wherein said transducers means sensing the backflow of blood, occurring upon blood vessel penetration, comprises:
means for detecting the physical properties of the blood as a fluid.

62. The device of claim 7 wherein said transducers means sensing the backflow of blood, occurring upon blood vessel penetration, comprises:
acoustic sensing means.

63. The device of claim 7 wherein said transducers means sensing the backflow of blood, occurring upon blood vessel penetration, comprises:
means for sensing ultrasound.

64. The device of claim 7 wherein said transducers means sensing the backflow of blood, occurring upon blood vessel penetration, comprises:
pressure sensing means.

65. The device of claim 7 wherein said transducers means sensing the backflow of blood, occurring upon blood vessel penetration, comprises:
means for detecting chemical properties of the blood.

66. The device of claim 7 wherein said transducers means sensing the backflow of blood, occurring upon blood vessel penetration, comprises:
means for identifying blood presence by detecting blood components.

67. The device of claim 2 wherein said means for self-propelled advancement of said intravascular catheter advances said catheter to a predetermined advanced position into the interior of a blood vessel.

68. The intravascular catheter placement device of claim 83 further comprising:
a chamber, wherein the pressure within said chamber is a partial vacuum pressure, said chamber being in communication with said hollow needle.

69. The device of claim 1 further comprising:
a chamber, wherein the pressure within said chamber is below the atmospheric pressure, said chamber being in communication with said hollow needle.

70. The device of claim 1 further comprising:
a chamber in communication with said hollow needle, said chamber being adapted to sealable closure upon body tissues sealing of said hollow needle.

71. The device of claim 1 further comprising:
side wall means for defining a blood-receiving chamber having an opening in communication with said hollow needle, through which blood is receivable into said chamber, said chamber including at least one displaceable member to change the volume within said chamber.

72. The device of claim 1 further comprising:
side wall means for defining a blood-receiving chamber having an opening in communication with said hollow needle, through which blood is receivable into said chamber, said chamber including at least one deformable member to change the pressure within said chamber.

73. The device of claim 1 further comprising:
means for applying a suction to said hollow needle to cause said propelling means to advance the intravascular catheter upon blood vessel penetration by said hollow needle.

74. The device of claim 1 further comprising:
means for accelerating the backflow response time upon blood vessel penetration to cause said propelling means to advance the intravascular catheter immediately upon blood vessel penetration by said hollow needle.

75. The device of claim 1, further comprising:
means for enhancing the pressure differential between the pressure within the blood vessel and the atmospheric pressure within a chamber in communication with said blood vessel via said hollow needle.

76. The device of claim 1 further comprising:
means sensing backflow of blood, occurring upon blood vessel penetration, to automatically release locking means releasably retaining said intravascular catheter in a retracted position to actuate said propelling means to automatically advance said intravascular catheter.

77. The device of claim 76 wherein said sensing means includes transducers which activates an electromagnet to automatically actuate said self-propelling means, upon blook vessel penetration.

78. The device of claim 1 wherein said means for self-propelled advancement of said intravascular catheter advances said catheter to a predetermined advanced position into the interior of a blood bessel.

79. The device of claim 1 further comprising:
actuating means to actuate said means for said self-propelled advancement of said catheter.

80. The device of claim 1, further comprising:
means for sensing pressure differential between the pressure within a penetrated blood vessel and the pressure within a chamber in communication with said blood vessel via said hollow needle, said means for sensing pressure differential being responsive thereto to automatically advance said catheter.

81. The device of claim 1 further comprising:
side wall means for definign a blood-receiving chamber having an opening in communication with said hollow needle, through which blood is receivable into said chamber, said chamber including at least one displaceable member, said displaceable member being displaceable in response to pressure changes occurring within said chamber, said displaceable member being responsive thereto to automatically advance said catheter.

82. The device of claim 1 further comprising:
side wall means for defining a blood-receiving chamber having an opening in communication with said hollow needle, through which blood is receivable into said chamber, said chamber including at least one deformable member, said deformable member being deformable in response to pressure changes occurring within said chamber, said deformable member being responsive thereto to automatically advance said catheter.

83. An intravascular catheter placement device for the insertion of intravascular catheter into the interior of a blood vessel comprising:
an intravascular catheter;
a hollow needle, said catheter being concentric to said hollow needle;
means for automatic initiation and advancement of said intravascular catheter to an advanced position into the interior of a blood vessel.

84. The device of claim 83 further comprising:
means for sensing penetration of a blood vessel and responsive thereto to automatically advance said catheter.

* * * * *

UNITED STATES PATENT AND TRADEMARK OFFICE
CERTIFICATE OF CORRECTION

PATENT NO. : 5,312,361  
DATED : May 17, 1994  
INVENTOR(S) : Filiberto P. Zadini, Giorgio C. Zadini It is certified that error appears in the above-indentified patent and that said Letters Patent is hereby corrected as shown below:

In Claim 1, column 17, line 28, please delete the phrase "self initialed and for", and replace it with --for self-initiated and--.

In claim 19, column 18, line 42, before the words "a housing", please delete the word "is".

In Claim 24, column 19, line 12, after the word "from", please delete the word "aneedle", and replace it with --a needle--.

In Claim 31, column 19, line 39, after the word "The", please delete the word "devioe" and replace it with --device--.

In Claim 32, column 19, line 54, after the words "thereto to", please delete the word "manually" and replace it with --automatically--.

UNITED STATES PATENT AND TRADEMARK OFFICE
CERTIFICATE OF CORRECTION

PATENT NO. : 5,312,361

DATED : May 17, 1994

INVENTOR(S) : Filibertol P. Zadini, Giorgio C. Zadini

It is certified that error appears in the above-indentified patent and that said Letters Patent is hereby corrected as shown below:

In Claim 37, column 20, line 35, after the word "creation", please delete the word "o.fvacuum" and replace with --of vacuum--.

In Claim 43, column 21, line 25, please delete the word "herein" and replace it with --wherein--.

In Claim 68, column 24, line 46, after the word "claim", please delete the numeral "83" and replace it with the numeral --1--.

In Claim 78, column 25, line 36, after the word "blood", please delete the word "bessel" and replace it with --vessel--.

In Claim 81, line 8, after the words "means for", please delete the word "definign" and replace it with --defining--.

Signed and Sealed this

Eighteenth Day of October, 1994

Attest:

BRUCE LEHMAN

Attesting Officer

Commissioner of Patents and Trademarks